United States Patent
Cockerill et al.

(10) Patent No.: US 6,174,889 B1
(45) Date of Patent: Jan. 16, 2001

(54) BICYCLIC HETEROAROMATIC COMPOUNDS AS PROTEIN TYROSINE KINASE INHIBITORS

(75) Inventors: George Stuart Cockerill, Bedford; Malcolm Clive Carter, Ware; Stephen Barry Guntrip, Hertford; Kathryn Jane Smith, Bishop's Stortford, all of (GB)

(73) Assignee: Glaxo Wellcome Inc., Research Triangle Park, NC (US)

(*) Notice: Under 35 U.S.C. 154(b), the term of this patent shall be extended for 0 days.

(21) Appl. No.: 09/214,270

(22) PCT Filed: Jul. 11, 1997

(86) PCT No.: PCT/EP97/03674

§ 371 Date: Dec. 31, 1998

§ 102(e) Date: Dec. 31, 1998

(87) PCT Pub. No.: WO98/02438

PCT Pub. Date: Jan. 22, 1998

(30) Foreign Application Priority Data

Jul. 13, 1996 (GB) .................................................. 9614763
Dec. 7, 1996 (GB) .................................................. 9625492

(51) Int. Cl.⁷ ........................ A61K 31/519; C07D 471/04
(52) U.S. Cl. ............... 514/258; 514/252.02; 514/255.05; 544/238; 544/279
(58) Field of Search ............................. 514/258, 252.02, 514/255.05; 544/253, 279, 238

(56) References Cited

U.S. PATENT DOCUMENTS 5,654,307 * 8/1997 Bridges et al. ...................... 514/258

FOREIGN PATENT DOCUMENTS

| 5 600 | 1/1968 | (FR) . |
| WO 95 19774 | 7/1995 | (WO) . |
| WO 97 13771 | 4/1997 | (WO) . |
| WO 97 18212 | 5/1997 | (WO) . |

OTHER PUBLICATIONS

D. L. Boger et al: "Regiocontrolled nucleophilic addition to selectively activated p–quinone diimines: alternative preparation of a key intermediate employed in the preparation of the CC–1065 left–hand subunit", Journal of Organic Chemistry, vol. 55, No. 4, 1990, Easton, US, pp. 1379–1390.

* cited by examiner

Primary Examiner—Richard L. Raymond
(74) Attorney, Agent, or Firm—John L. Lemanowicz

(57) ABSTRACT

Substituted heteroaromatic compounds, and in particular substituted bicyclic heteroaromatic compounds of formula (I), wherein X is N or CH; A represents a fused 5, 6 or 7-membered heterocyclic ring containing 1 to 5 heteroatoms which may be the same or different and which are selected from N, O or $S(O)_m$, wherein m is as defined above, the heterocyclic ring containing a total of 1, 2 or 3 double bonds inclusive of the bond in the pyridine or pyrimidine ring to which it is fused, with the provisos that the heterocyclic ring does not form part of a purine and that the fused heterocyclic ring does not contain two adjacent O or $S(O)_m$ atoms. U represents a 5 to 10-membered mono or bicyclic ring system in which one or more of the carbon atoms is optionally replaced by a heteroatom independently selected from N, O and $S(O)_m$, wherein m is 0, 1 or 2 and wherein the ring system is substituted by at least one independently selected $R^6$ group and is optionally substituted by at least one independently selected $R^4$ group, with the proviso that U does not represent phenyl; are protein tyrosine kinase inhibitors. The compounds are described as are methods for their preparation, pharmaceutical compositions including such compounds and their use in medicine, for example in the treatment of cancer and psoriasis.

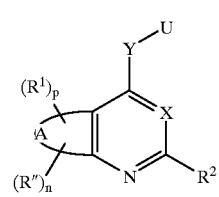

(I)

25 Claims, No Drawings

BICYCLIC HETEROAROMATIC COMPOUNDS AS PROTEIN TYROSINE KINASE INHIBITORS

This application is a 371 of PCT/EP97/03674, filed Jul. 11, 1997.

The present invention relates to a series of substituted heteroaromatic compounds, methods for their preparation, pharmaceutical compositions containing them and their use in medicine. In particular, the invention relates to bioisosteres of quinoline and quinazoline derivatives which exhibit protein tyrosine kinase inhibition.

Protein tyrosine kinases catalyse the phosphorylation of specific tyrosyl residues in various proteins involved in the regulation of cell growth and differentiation (A. F. Wilks, Progress in Growth Factor Research, 1990, 2, 97–111; S. A. Courtneidge, Dev. Supp.l, 1993, 57–64; J. A. Cooper, Semin. Cell Biol., 1994, 5(6), 377–387; R. F. Paulson, Semin. Immunol., 1995, 7(4), 267–277; A. C. Chan, Curr. Opin. Immunol., 1996, 8(3), 394–401). Protein tyrosine kinases can be broadly classified as receptor (e.g. EGFr, c-erbB-2, c-met, tie-2, PDGFr, FGFr) or non-receptor (e.g. c-src, lck, Zap70) kinases. Inappropriate or uncontrolled activation of many of these kinase, i.e. aberrant protein tyrosine kinase activity, for example by over-expression or mutation, has been shown to result in uncontrolled cell growth.

Aberrant activity of protein tyrosine kinases, such as c-erbB-2, c-src, c-met, EGFr and PDGFr have been implicated in human malignancies. Elevated EGFr activity has, for example, been implicated in non-small cell lung, bladder and head and neck cancers, and increased c-erbB-2 activity in breast, ovarian, gastric and pancreatic cancers. Inhibition of protein tyrosine kinases should therefore provide a treatment for tumours such as those outlined above.

Aberrant protein tyrosine kinase activity has also been implicated in a variety of other disorders: psoriasis, (Dvir et al, J. Cell. Biol; 991, 113, 857–865), fibrosis, atherosclerosis, restenosis, (Buchdunger et al, Proc. Natl. Acad. Sci. USA; 1991, 92, 2258–2262), auto-immune disease, allergy, asthma, transplantation rejection (Klausner and Samelson, Cell; 1991, 64, 875–878), inflammation (Berkois, Blood; 1992, 79(9), 2446–2454), thrombosis (Salari et al, FEBS; 1990, 263(1), 104–108) and nervous system diseases (Ohmichi et al, Biochemistry, 1992, 31, 4034–4939). Inhibitors of the specific protein tyrosine kinases involved in these diseases eg PDGF-R in restenosis and EGF-R in psoriasis, should lead to novel therapies for such disorders. P56lck and zap 70 are indicated in disease conditions in which T cells are hyperactive e.g. rheumatoid arthritis, autoimmune disease, allergy, asthma and graft rejection. The process of angiogenesis has been associated with a number of disease states (e.g. tumourogenesis, psoriasis, rheumatoid arthritis) and this has been shown to be controlled through the action of a number of receptor tyrosine kinases (L. K. Shawver, DDT, 1997, 2(2), 50–63).

EP0635507 discloses a class of tricyclic quinazoline derivatives of the formula:

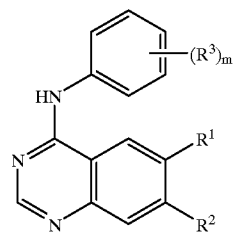

wherein $R^1$ and $R^2$ together form specified optionally substituted groups containing at least one heteroatom so as to form a 5 or 6-membered ring, in which there is a N atom at the 6 position of the quinazoline ring; $R^3$ includes independently hydrogen, hydroxy, halogeno, (1–4C)alkyl, (1–4C) alkoxy di-[(1–4C)alkyl]amino, or (2–4C)alkanoylamino. The above citation notes that receptor tyrosine kinases in general, which are important in the transmission of biochemical signals initiating cell replication, are frequently present at increased levels or with higher activities in common human cancers such as breast cancer (Sainsbury et al, Brit, J. Cancer, 1988, 58, 458). It is suggested that inhibitors of receptor tyrosine kinase should be of value as inhibitors of the growth of mammalian cancer cells (Yaish et al. Science, 1988, 242, 933). This citation therefore has the aim of providing quinazoline derivatives which inhibit receptor tyrosine kinases involved in controlling the tumourigenic phenotype.

WO 95/15758 discloses aryl and heteroaryl quinazoline derivatives of formula

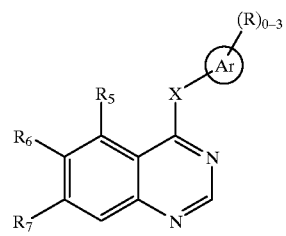

wherein X includes a bond, O, S, SO, $SO_2$, C≡C, C=C, $CH_2$ and NH; Ar includes phenyl, naphthyl, naphthalenyl, indolyl, pyridyl, piperidinyl, piperazinyl, dinydroquinolinyl, tetrahydroquinolinyl, thienyl, indanyl, pyrazolyl and 1,4-benzodioxanyl; and $R_5$, $R_6$ and $R_7$ independently include hydrogen, alkyl, alkylthio, cycloalkyl, hydroxy, alkoxy, aralkoxy, aryl, halo, haloalkyl, carboxy or carbalkoxy; as inhibitors of CSF-1R and/or p56lck receptor tyrosine kinase activity.

WO 95/19774 discloses bicyclic derivatives of formula:

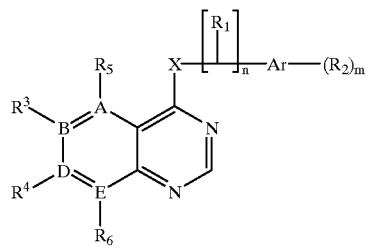

in which A to E are nitrogen or carbon and at least one of A to E is nitrogen; or two adjacent atoms together are N, O or S; $R_1$ is H or alkyl and n is 0, 1 or 2; m is 0 to 3 and $R_2$ includes optionally substituted alkyl, alkoxy, cycloalkoxy, cycloalkoxy, or two $R_2$ groups together form a carbocycle or heterocycle. The compounds are said to inhibit epidermal growth factor receptor tyrosine kinase and suggested uses include the treatment of cancer, psoriasis, kidney disease, pancreatitis and contraception.

WO 96/07657 discloses pyrimido[5,4-d]pyrimidine derivatives of formula

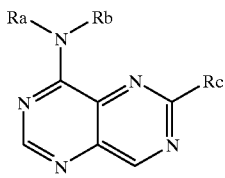

wherein Ra includes hydrogen or alkyl; Rb includes optionally substituted phenyl; and Rc includes hydrogen, halo, alkyl, cycloalyl, cycloalkylalkylanyl, aralkyl, OH, optionally substituted alkoxy, cycloalkoxy, aryloxy, aralkoxy, mercapto, optionally substituted alkyl- or arysulfenyl, -sulfinyl, or -sulfonyl and substituted alkyleneimino; as EGF-R inhibitors.

WO 96/09294 discloses quinoline and quinazoline derivatives of formula

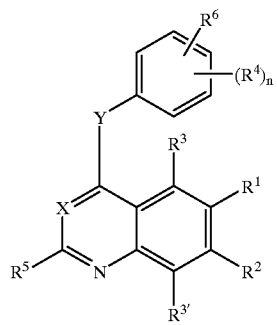

wherein X is N or CH; Y includes O, S, $CH_2O$ and NH; $R^6$ includes phenoxy, benzylozy, benzylmercapto, benzylamino, benzyl, anilino, benzoyl, anilinocarbonyl, anilnomethyl, phenylethynyl, phenylethenyl, phenylethyl, phenylthio, phenylsulphonyl, benzylthio, benzylsulphonyl, phenylthiomethyl, phenylsulphonylmethyl, phenoxymethyl, thienylmethoxy, furanylmethoxy, cyclohexyl, and cyclohexylmethoxy; and $R^1$, $R^2$, $R^3$ and $R^{3'}$ include a range of possible substituents, predominantly not including heterocyclic ring systems; as protein receptor tyrosine kinase inhibitors, in particular as c-erbB-2 and/or p56lck inhibitors.

WO 96/15118 discloses quinazoline derivatives of formula

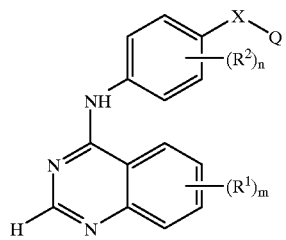

wherein X includes O, S, SO, $SO_2$, $CH_2$, $OCH_2$, $CH_2O$ and CO; Q includes a phenyl or naphthyl group and various 5- or 6-membered heteroaryl moieties; n is 0, 1, 2 or 3 and each $R^2$ is independently halogeno, trifluoromethyl, hydroxy, amino, nitro, cyano, $C_{1-4}$ alkyl, $C_{1-4}$ alkoxy, $C_{1-4}$ alkylamino, $diC_{1-4}$ alkyl amino or $C_{2-4}$ alkanoylamino; m is 1, 2 or 3 and $R^1$ includes a range of possible substituents, predominantly not including heterocyclic ring systems; as receptor tyrosine kinase inhibitors, in particular as EGF-R inhibitors.

WO 96/15128 discloses pyrido[2,3-d]pyrimidine and naphthyridine derivatives of formula

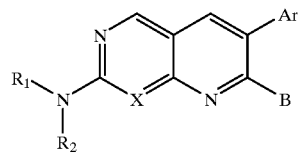

wherein X is CH or N; B is halo, hydroxy or $NR_3R_4$; Ar includes unsubstituted and substituted phenyl or pyridyl; and $R_1$, $R_2$, $R_3$ and $R_4$ independently include hydrogen, amino, $C_{1-8}$alkylamino, di-$C_{1-8}$alkylamino, unsubstituted and substituted aromatic or heteroaromatic groups, and unsubstituted and substituted $C_{1-8}$alkyl, $C_{2-8}$alkenyl or $C_{2-8}$alkynyl groups.

WO 96/16960 discloses quinazoline derivatives of formula

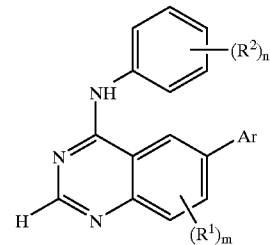

wherein m is 1 or 2; each $R^1$ independently includes hydrogen and $C_{1-4}$alkoxy; n is 1, 2 or 3; each $R^2$ independently includes hydrogen, halogeno and $C_{1-4}$alkyl, or $R^2$ is an aryl- or heteroaryl-containing group, including pyridylmethoxy and benzoyl; and Ar includes a substituted or unsubstituted 5- or 9-membered nitrogen-linked heteroaryl moiety containing up to four nitrogen atoms, in particular imidazol-1-yl, imidazolin-1-yl, benzimidazol-1-yl, pyrazol-1-yl and 1,2,4-triazol-1-yl; as receptor tyrosine kinase inhibitors, in particular as EGF-R inhibitors.

It is therefore a general object of the present invention to provide compounds suitable for the treatment of disorders mediated by protein tyrosine kinase activity, and in particular treatment of the above mentioned disorders.

In addition to the treatment of tumours, the present invention envisages that other disorders mediated by protein tyrosine kinase activity may be treated effectively by inhibition, including preferential inhibition, of the appropriate protein tyrosine kinase activity.

Broad spectrum inhibition of protein tyrosine kinase may not always provide optimal treatment of, or example tumours, and could in certain cases even be detrimental to subjects since protein tyrosine kinases provide an essential role in the normal regulation of cell growth.

It is another object of the present invention to provide compounds which preferentially inhibit protein tyrosine kinases, such as EGFr, c-erbB-2, c-erbB-4, c-met, tie-2, PDGFr, c-src, lck, Zap70, and fyn. There is also perceived to be a benefit in the preferential inhibition involving small groups of protein tyrosine kinases, for example c-erbB-2 and c-erbB-4 or c-erbB-2, c-erbB-4 and EGF-R.

A further object of the present invention is to provide compounds useful in the treatment of protein tyrosine kinase related diseases which minimise undesirable side-effects in nthe recipient.

The present invention relates to heterocyclic compounds which may be used to treat disorders mediated by protein tyrosine kinases and in particular have anti-cancer properties. More particularly, the compounds of the present invention are potent inhibitors of protein tyrosine kinases such as such as EGFr, c-erbB-2, c-erbB-4, c-met, tie-2, PDGFr, c-src, lck, Zap70, and fyn, thereby allowing clinical management of particular diseasesd tissues.

The present invention envisages, in particular, the treatment of human malignancies, for example breast, non-small cell lung, ovary, stomach, and pancreatic tumours, especially those driven by EGFr or erbB-2, using the compounds of the present invention. For example, the invention includes compounds which are highly active against the c-erbB-2 protein tyrosine kinase often in preference to the EGF receptor kinase hence allowing treatment of c-erbB-2 driven tumours. However, the invention also includes compounds which are highly active against both c-erbB-2 and EGF-R receptor kinases hence allowing treatment of a broader range of tumours.

More particularly, the present invention envisages that disorders mediated by protein tyrosine kinase activity may be treated effectively by inhibition of the appropriate protein tyrosine kinase activity in a relatively selective manner, thereby minimising potential side effects.

Accordingly, the present invention provides a compound of formula (I):

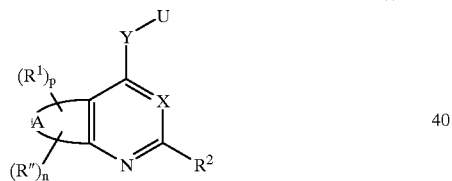

or a salt thereof;
wherein X is N or CH;
Y is a group W(CH$_2$), (CH$_2$)W, or W, in which W is O, S(O)$_m$ wherein m is 0, 1 or 2, or NR$^a$ wherein R$^a$ is hydrogen or a C$_{1-8}$ aklyl group;
R" represents a phenyl group or a 5- or 6-membered heterocyclic ring containing 1 to 4 heteroatoms selected from N, O or S(O)$_m$, wherein m is as defined above, with the proviso that the ring does not contain two adjacent O or S(O)$_m$ atoms, the phenyl group or the heterocyclic ring being optionally substituted by one or more R$^1$ groups; and n=0 or 1;
each R$^1$ is independently selected from the group comprising amino, hydrogen, halogen, hydroxy, nitro, carboxy, formyl, cyano, trifluoromethyl, trifluoromethoxy, carbamoyl, ureido, guanidino, C$_{1-8}$ alkyl, C$_{1-8}$ alkoxy, C$_{3-8}$ cycloalkoxy, C$_{4-8}$ alkylcycloalkoxy, C$_{1-8}$ alkylcarbonyl, C$_{1-8}$ alkoxycarbonyl, N-C$_{1-4}$ alkylcarbamoyl, N,N-di-[C$_{1-4}$ alkyl]carbamoyl, hydroxyamino, C$_{1-4}$ alkoxyamino, C$_{2-4}$ alkanoyloxyamino, C$_{1-4}$ alkylamino, di[C$_{1-4}$ alkyl] amino, di-[C$_{1-4}$ alkyl]amino-C$_{1-4}$ alkylene-(C$_{1-4}$ alkyl) amino, C$_{1-4}$ alkylamino-C$_{1-4}$ alkylene-(C$_{1-4}$ alkyl) amino, hydroxy-C$_{1-4}$ alkylene-(C$_{1-4}$ akyl)amino, phenyl, phenoxy, 4-pyridon-1-yl, pyrrolidin-1-yl, imidazol-1-yl, piperidino, morpholino, thiomorpholino, thiomorpholino-1-oxide, thiomorpholino-1,1-dioxide, piperazin-1-yl, 4-C$_{1-4}$ alkylpiperazin-1-yl, dioxolanyl, C$_{1-8}$ alkylthio, arylthio, C$_{1-4}$ alkylsulphinyl, C$_{1-4}$ alkylsulphonyl, arylsulphinyl, arylsulphonyl, halogeno-C$_{1-4}$ alkyl, hydroxy-C$_{1-4}$ alkyl, C$_{2-4}$ alkanoyloxy-C$_{1-4}$ alkyl, C$_{1-4}$ alkoxy-C$_{1-4}$ alkyl, carboxy-C$_{1-4}$ alkyl, formyl-C$_{1-4}$ alkyl, C$_{1-4}$ alkoxycarbonyl-C$_{1-4}$-alkyl, carbamoyl-C$_{1-4}$ alkyl, N-C$_{1-4}$ alkylcarbamoyl-C$_{1-4}$alkyl, N,N-di-[C$_{1-4}$ alkyl]carbamoyl-C$_{1-4}$alkyl, amino-C$_{1-4}$ alkyl, C$_{1-4}$ alkylamino-C$_{1-4}$ alkyl, di-[C$_{1-4}$ alkyl]amino-C$_{1-4}$ alkyl, phenyl-C$_{1-4}$ alkyl, 4-pyridon-1-yl-C$_{1-4}$ alkyl, pyrrolidin-1-yl-C$_{1-4}$ alkyl, imidazol-1-yl-C$_{1-4}$ alkyl, piperidino-C$_{1-4}$ alkyl, morpholino-C$_{1-4}$ alkyl, thiomorpholino-C$_{1-4}$alkyl, thiomorpholino-1-oxide-C$_{1-4}$alkyl, thiomorpholino-1,1-dioxide-C$_{1-4}$alkyl, piperazin-1-yl-C$_{1-4}$alkyl, 4-C$_{1-4}$ alkylpiperazin-1-yl-C$_{1-4}$ alkyl, hydroxy-C$_{2-4}$ alkoxy-C$_{1-4}$ alkyl, C$_{1-4}$ alkoxy-C$_{2-4}$ alkoxy-C$_{1-4}$ alkyl, hydroxy-C$_{2-4}$ alkylamino-C$_{1-4}$ alkyl, C$_{1-4}$ alkoxy-C$_{2-4}$ alkylamino-C$_{1-4}$ alkyl, C$_{1-4}$ alkylthio-C$_{1-4}$ alkyl, hydroxy-C$_{2-4}$ alkylthio-C$_{1-4}$ alkyl, C$_{1-4}$ alkoxy-C$_{2-4}$ alkylthio-C$_{1-4}$ alkyl, phenoxy-C$_{1-4}$ alkyl, anilino-C$_{1-4}$ alkyl, phenylthio-C$_{1-4}$ alkyl, cyano-C$_{1-4}$ alkyl, halogeno-C$_{2-4}$ alkoxy, hydroxy-C$_{2-4}$ alkoxy, C$_{2-4}$ alkanoyloxy-C$_{2-4}$ alkoxy, C$_{1-4}$ alkoxy-C$_{2-4}$ alkoxy, carboxy-C$_{1-4}$ alkoxy, formyl-C$_{1-4}$ alkoxy, C$_{1-4}$ alkoxycarbonyl-C$_{1-4}$ alkoxy, carbamoyl-C$_{1-4}$ alkoxy, N-C$_{1-4}$ alkylcarbamoyl-C$_{1-4}$ alkoxy, N,N-di-[C$_{1-4}$ alkyl]carbamoyl-C$_{1-4}$ alkoxy, amino-C$_{2-4}$ alkoxy, C$_{1-4}$ alkylamino-C$_{2-4}$ alkoxy, di-[C$_{1-4}$ alkyl]amino-C$_{2-4}$ alkoxy, di-[C$_{1-4}$ alkyl-C$_{2-4}$ alkoxy]amino-C$_{2-4}$ alkoxy, C$_{2-4}$ alkanoyloxy, hydroxy-C$_{2-4}$ alkanoyloxy, C$_{1-4}$alkoxy-C$_{2-4}$ alkanoyloxy, phenyl-C$_{1-4}$ alkoxy, phenoxy-C$_{2-4}$ alkoxy, anilino-C$_{2-4}$ alkoxy, phenylthio-C$_{2-4}$ alkoxy, 4-pyridon-1-yl-C$_{2-4}$ alkoxy, piperidino-C$_{2-4}$ alkoxy, pyrrolidin-1-yl-C$_{2-4}$ alkoxy, imidazol-1-yl-C$_{2-4}$ alkoxy, morpholino-C$_{2-4}$ alkoxy, thiomorpholino-C$_{2-4}$ alkoxy, thiomorpholino-1-oxide-C$_{2-4}$ alkoxy, thiomorpholino-1,1-dioxide-C$_{2-4}$ alkoxy, piperazin-1-yl-C$_{2-4}$ alkoxy, 4-C$_{1-4}$ alkylpiperazin-1-yl-C$_{2-4}$ alkoxy, halogeno-C$_{2-4}$ alkylamino, hydroxy-C$_{2-4}$ alkylamino, C$_{2-4}$ alkanoyloxy-C$_{2-4}$ alkylamino, C$_{1-4}$ alkoxy-C$_{2-4}$ alkylamino, carboxy-C$_{1-4}$ alkylamino, C$_{1-4}$ alkoxycarbonyl-C$_{1-4}$ alkylamino, carbamoyl-C$_{1-4}$ alkylamino, N-C$_{1-4}$ alkylcarbamoyl-C$_{1-4}$ alkylamino, N,N-di-[C$_{1-4}$ alkyl]carbamoyl-C$_{1-4}$ alkylamino, amino-C$_{2-4}$ alkylamino, C$_{1-4}$ alkylamino-C$_{2-4}$ alkylamino, di-[C$_{1-4}$alkyl]amino-C$_{2-4}$ alkylamino, phenyl-C$_{1-4}$ alkylamino, phenoxy-C$_{2-4}$ alkylamino, anilino-C$_{2-4}$ alkylamino, 4-pyridon-1-yl-C$_{2-4}$ alkylamino, pyrrolidin-1-yl-C$_{2-4}$ alkylamino, imidazol-1-yl-C$_{2-4}$ alkylamino, piperidino-C$_{2-4}$ alkylamino, morpholino-C$_{2-4}$ alkylamino, thiomorpholino-C$_{2-4}$ alkylamino, thiomorpholino-1-oxide-C$_{2-4}$ alkylamino, thiomorpholino-1,1-dioxide-C$_{2-4}$ alkylamino, piperazin-1-yl-C$_{2-4}$ alkylamino, 4-(C$_{1-4}$ alkyl) piperazin-1-yl-C$_{2-4}$ alkylamino, phenylthio-C$_{2-4}$ alkylamino, C$_{2-4}$ alkanoylamino, C$_{1-4}$ alkoxycarbonylamino, C$_{1-4}$ alkylsulphonylamino, C$_{1-4}$ alkylsulphinylamino, benzamido, benzenesulphonamido, 3-phenylureido, 2-oxopyrrolidin-1-yl, 2,5-dioxopyrrolidin-1-yl, halogeno-C$_{2-4}$ alkanoylamino, hydroxy-C$_{2-4}$ alkanoylamino, hydroxy-$C_{2-4}$ alkanoyl-($C_{1-4}$ alkyl) amino, $C_{1-4}$ alkoxy-$C_{2-4}$ alkanoylamino, carboxy-$C_{2-4}$ alkanoylamino, $C_{1-4}$ alkoxycarbonyl-$C_{2-4}$ alkanoylamino, carbamoyl-$C_{2-4}$ alkanoylamino, N-$C_{1-4}$ alkylcarbamoyl-$C_{2-4}$ alkanoylamino, N,N-di-[$C_{1-4}$ alkyl]carbamoyl-$C_{2-4}$ alkanoylamino, amino-$C_{2-4}$ alkanoylamino, $C_{1-4}$ alkylamino-$C_{2-4}$ alkanoylamino or di-[$C_{1-4}$ alkyl]amino-$C_{2-4}$ alkanoylamino, and wherein said benzamido or benzenesulphonamido substituent or any anilino, phenoxy or phenyl group on a $R^1$ substituent may optionally bear one or two halogeno, $C_{1-4}$ alkyl or $C_{1-4}$ alkoxy substituents; and wherein any substituent containing a heterocyclic ring may optionally bear one or two halogeno, $C_{1-4}$ alkyl or $C_{1-4}$ alkoxy substituents on said ring; and wherein any substituent containing a heterocyclic ring may optionally bear one or two oxo or thioxo substituents on said ring;

or $R^1$ represents a group selected from $M^1$-$M^2$-$M^3$-$M^4$, $M^1$-$M^5$ or $M^1$-$M^2$-$M^{3'}$-$M^6$ wherein $M^1$ represents a $C_{1-4}$ alkyl group, wherein optionally a $CH_2$ group is replaced by a CO group;

$M^2$ represents $NR^{12}$ or $CR^{12}R^{13}$, in which $R^{12}$ and $R^{13}$ each independently represent H or $C_{1-4}$ alkyl;

$M^3$ represents a $C_{1-4}$ alkyl group;

$M^{3'}$ represents a $C_{1-4}$ alkyl group or is absent;

$M^4$ represents CN, $NR^{12}S(O)_mR^{13}$, $S(O)_mNR^{14}R^{15}$, $CONR^{14}R^{15}$, $S(O)_mR^{13}$ or $CO_2R^{13}$, in which $R^{12}$, $R^{13}$ and m are as hereinbefore defined and $R^{14}$ and $R^{15}$ each independently represent H or $C_{1-4}$ alkyl, or $R^{14}$ and $R^{15}$ together with the nitrogen atom to which they are attached represent a 5- or 6-membered ring optionally containing 1 or 2 additional heteroatoms selected from N, O or $S(O)_m$ in which ring any nitrogen atom present may optionally be substituted with a $C_{1-4}$ alkyl group, and which ring may optionally bear one or two oxo or thioxo substituents;

$M^5$ represents the group $NR^{14}R^{15}$, wherein $R^{14}$ and $R^{15}$ are as defined above, or $M^5$ represents the group

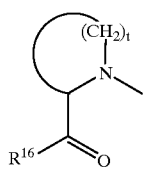

in which t represents 2 to 4 and $R^{16}$ represents OH, $OC_{1-4}$ alkyl or $NR^{14}R^{15}$; and $M^6$ represents a $C_{3-6}$ cycloalkyl group, the group $NR^{14}R^{15}$, wherein $R^{14}$ and $R^{15}$ are as defined above, or a 5- or 6-membered heterocyclic ring system containing 1 to 4 heteroatoms selected from N, O or S;

and p is 0 to 3; or when p is 2 or 3, two adjacent $R^1$ groups together form an optionally substituted methylenedioxy or ethylenedioxy group;

$R^2$ is selected from the group comprising hydrogen, halogen, trifluoromethyl, $C_{1-4}$ alkyl and $C_{1-4}$ alkoxy;

U represents a 5 to 10-membered mono or bicyclic ring system in which one or more of the carbon atoms is optionally replaced by a heteroatom independently selected from N, O and $S(O)_m$, wherein m is 0, 1 or 2 and wherein the ring system is substituted by at least one independently selected $R^6$ group and is optionally substituted by at least one independently selected $R^4$ group, with the proviso that U does not represent phenyl;

each $R^4$ is independently hydrogen, hydorxy, halogen, $C_{1-4}$ alkyl, $C_{1-4}$ alkoxy, $C_{1-4}$ alkylamino, di-[$C_{1-4}$ alkyl] amino, $C_{1-4}$ alkylthio, $C_{1-4}$ alkylsulphinyl, $C_{1-4}$ alkylsulphonyl, $C_{1-4}$ alkylcarbonyl, $C_{1-4}$ alkylcarbamoyl, di-[$C_{1-4}$ alkyl]carbamoyl, carbamyl, $C_{1-4}$ alkoxycarbonyl, cyano, nitro or trifluoromethyl;

each $R^6$ is independently a group $ZR^7$ wherein Z is joined to $R^7$ through a $(CH_2)p$ group in which p is 0, 1 or 2 and Z represents a group $V(CH_2)$, $V(CF_2)$, $(CH_2)V$, $(CF_2)V$, $V(CRR')$, $V(CHR)$ or V where R and R' are each $C_{1-4}$ alkyl and in which V is a hydrocarby group containing 0,1 or 2 carbon atoms, carbonyl, dicarbonyl, CH(OH), CH(CN), sulphonamide, amide, O, $S(O)_m$ or $NR^b$ where $R^b$ is hydrogen or $R^b$ is $C_{1-4}$ alkyl; and $R^7$ is an optionally substituted $C_{306}$ cycloalkyl; or an optionally substituted 5, 6, 7, 8, 9 or 10-membered carbocyclic or heterocyclic moiety;

or $R^6$ is a group $ZR^7$ in which Z is $NR^b$, and $NR^b$ and $R^7$ together form an optionally substituted 5, 6, 7, 8, 9 or 10-membered carbocyclic or heterocyclic moiety;

A represents a fused 5, 6 or 7-membered heterocyclic ring containing 1 to 5 heteroatoms which may be the same or different and which are selected from N, O or $S(O)_m$, wherein m is as defined above, the heterocyclic ring containing a total of 1, 2 or 3 double bonds inclusive of the bond in the pyridine or pyrimidine ring to which it is fused, with the provisos that the heterocyclic ring does not form part of a purine and that the fused heterocyclic ring does not contain two adjacent O or $S(O)_m$ atoms.

Solvates of the compounds of formula (I) are also included within the scope of the present invention.

Heterocyclic groups comprise one or more rings which may be saturated, unsaturated, or aromatic and which may independently contain one or more heteroatoms in each ring.

Carbocyclic groups comprise one or more rings which may be independently saturated, unsaturated, or aromatic and which contain only carbon and hydrogen.

Suitably the 5, 6, 7, 8, 9 or 10-membered heterocyclic moiety is selected from the group comprising: furan, dioxolane, thiophene, pyrrole, imidazole, pyrrolidine, pyran, pyridine, pyrimidine, morpholine, piperidine, oxazole, isoxazole, oxazoline, oxazolidine, thiazole, isothiazole, thiadiazole, benzofuran, indole, isoindole, quinazoline, quinoline, isoquinoline and ketal.

Suitably the 5, 6, 7, 8, 9 or 10-membered carbocyclic moiety is selected from the group comprising: phenyl, benzyl, indene, naphthalene, tetralin, decalin, cyclopentyl, cyclopentenyl, cyclohexyl, cyclohexenyl and cycloheptyl.

By halo is meant fluoro, chloro, bromo or iodo.

Alkyl groups containing three or more carbon atoms may be straight, branched or cyclised.

In an embodiment $R^1$ is as defined above with the exception of wherein any substituent containing a heterocyclic ring bears one or two oxo or thioxo substituents on said ring; and $R^{14}$ and $R^{15}$ are as defined above with the exception of wherein they together with the nitrogen atom to which they are attached represent a 5- or 6-membered ring and said ring bears one or two oxo or thioxo substituents; save that $R^1$ may represent 4-pyridon-1-yl, 4-pyridon-1-yl-$C_{1-4}$ alkyl, 4-pyridon-1-yl-$C_{2-4}$ alkoxy, 4-pyridon-1-yl-$C_{2-4}$ alkylamino, 2-oxopyrrolidin-1-yl or 2,5-dioxopyrrolidin-1-yl.

In an embodiment, X is N.

In a further embodiment, Y is $NR^b$, $NR^b(CH_2)$, or $(CH_2)NR^b$, preferably Y is $NR^b$ and $R^b$ is preferably hydrogen or methyl.

In a further embodiment R" is a 5- or 6-membered heterocyclic ring as defined above, optionally substituted by one or more $R^1$ groups selected from the group comprising amino, hydrogen, halogen, hydroxy, formyl, carboxy, cyano, nitro, $C_{1-8}$ alkyl, $C_{1-8}$ alkoxy, $C_{1-8}$ alkylthio, $C_{1-8}$ alkylsulphinyl, $C_{1-8}$ alkylsulphonyl, $C_{1-4}$ alkylamino, $C_{1-4}$ dialkylamino, dioxolanyl, hydroxy-$C_{1-4}$ alkyl or hydroxy-$C_{1-4}$ alkanoyl-($C_{1-4}$ alkyl)-amino.

In a further embodiment, n is 0 and each $R^1$ is selected from the group comprising amino, hydrogen, halogen, hydroxy, formyl, carboxy, cyano, nitro, $C_{1-8}$ alkyl, $C_{1-8}$ alkoxy, $C_{1-8}$ alkylthio, $C_{1-8}$ alkylsulphinyl, $C_{1-8}$ alkylsulphonyl, $C_{1-4}$ alkylamino, $C_{1-4}$ dialkylamino, dioxolanyl, benzyloxy or hydroxy-$C_{1-4}$ alkanoyl-($C_{1-4}$ alkyl)-amino.

In a preferred embodiment, n is 0, p is 1 and $R^1$ is selected from the group comprising amino, $C_{1-4}$ alkylamino, di$C_{1-4}$ alkylamino, especially di$C_{1-4}$ alkylamino, most especially dimethylamino or methylethylamino.

In a further embodiment, n is 0 and $R^1$ is selected from $M^1$-$M^2$-$M^3$-$M^4$, $M^1$-$M^5$ or $M^1$-$M^2$-$M^{3'}$-$M^6$ as defined above; and p=1.

In a further embodiment R" is a 5- or 6-membered heterocyclic ring as defined above substituted with an $R^1$ group selected from $M^1$-$M^2$-$M^3$-$M^4$, $M^1$-$M^5$ or $M^1$-$M^2$-$M^{3'}$-$M^6$ as defined above; and p=0.

In a further embodiment the group $M^2$-$M^3$-$M^4$ represents an α-, β- or γ-amino carboxylic, sulphinic or sulphonic acid or a $C_{1-4}$ alkyl ester, an amide or a $C_{1-4}$ alkyl- or di-($C_{1-4}$ alkyl)-amide thereof.

Preferably $M^1$ represents $CH_2$, CO, $CH_2CH_2$ or $CH_2CO$, more preferably $CH_2$.

Preferably $M^2$ represents $NR^{12}$ in which $R^{12}$ is as defined above; more preferably $R^{12}$ represents H or methyl.

Preferably $M^3$ represents $CH_2$, $CH_2CH_2$ or propyl.

Preferably $M^{3'}$ represents $CH_2$, ethyl, propyl, isopropyl or is absent.

Preferably $M^4$ represents $SOR^{13}$, $SO_2R^{13}$, $NR^{12}SO_2R^{13}$, $CO_2R^{13}$ or $CONR^{14}R^{15}$ in which $R^{12}$ and $R^{13}$ are defined above and $R^{14}$ and $R^{15}$ each independently represent H or $C_{1-4}$ alkyl; more preferably $R^{12}$, $R^{13}$, $R^{14}$ and $R^{15}$ each independently represent H or methyl.

Preferably $M^5$ represents a group $NR^{14}R^{15}$ in which $R^{14}$ and $R^{15}$ together with the nitrogen atom to which they are attached represent a 6-membered ring optionally containing an additional heteroatom selected from N or O, in which ring any nitrogen atom present may optionally be substituted with a $C_{1-4}$ alkyl group, preferably a methyl group; or $M^5$ represents a group

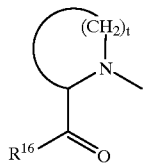

in which t represents 2 or 3 and $R^{16}$ represents OH, $NH_2$, $N(C_{1-4}$ alkyl$)_2$ or $OC_{1-4}$ alkyl; more preferably $R^{16}$ represents $NH_2$ or $N(CH_3)_2$.

$M^5$ also preferably represents a group $NR^{14}R^{15}$ in which $R^{14}$ and $R^{15}$ each independently represent hydrogen or $C_{1-4}$ alkyl, more preferably hydrogen, methyl, ethyl or isopropyl.

Preferably $M^6$ represents a group $NR^{14}R^{15}$ in which $R^{14}$ and $R^{15}$ each independently represent $C_{1-4}$ alkyl, more preferably methyl, or $R^{14}$ and $R^{15}$ together with the nitrogen atom to which they are attached represent a 5- or 6-membered ring optionally containing an additional heteroatom selected from N or O, in which ring any nitrogen atom present may optionally be substituted with a $C_{1-4}$ alkyl group, preferably a methyl group; or $M^6$ represents a 5- or 6-membered heterocyclic ring system containing 1 or 2 heteroatoms selected from N or O.

In a further preferred embodiment $M^2$-$M^3$-$M^4$ represents an α-amino carboxylic acid or a methyl ester or amide thereof.

In a further preferred embodiment $M^2$-$M^3$-$M^4$ represents an α-, β- or γ-amino sulphinic or sulphonic acid, more preferably a β- or γ-amino sulphinic or sulphonic acid, most preferably a β-aminosulphonic acid, or a methyl ester thereof.

In an especially preferred embodiment $M^2$-$M^3$-$M^4$ represents a methylsulphonylethylamino, methylsulphinylethylamino, methylsulphonylpropylamino, methylsulphinylpropylamino, methylsulphonamidoethylamino, sarcosinamide, glycine, glycinamide, glycine methyl ester or acetylaminoethylamino group.

In a further especially preferred embodiment $M^5$ represents a piperazinyl, methylpiperazinyl, piperidinyl, prolinamido or N,N-dimethylprolinamido group.

In a further especially preferred embodiment $M^5$ represents an isopropylamino or N-morpholinyl group.

In a further especially preferred embodiment $M^1$-$M^5$ represents an isopropylacetamido or N-morpholinoacetamido group.

In a further especially preferred embodiment $M^2$-$M^{3'}$-$M^6$ represents a pyridylamino, cyclopropylamino, N-(piperidin-4-yl)-N-methylamino, N,N-dimethylaminoprop-2-ylamino, N-(2-dimethylaminoethyl)-N-ethylamino or tetrahydrofuranomethylamino group, preferably a pyridylamino group.

In an embodiment R" may be selected from the group comprising phenyl, furan, thiophene, pyridine, pyrimidine, pyrazine, pyrrole, oxazole, isoxazole, oxadiazole, thiazole, isothiazole, triazole, tetrazole and imidazole or a hydrogenated derivative of any of the aforementioned.

In a further preferred embodiment R" may be selected from the group comprising phenyl, furan, imidazole, tetrazole, triazole, pyrrolidine, piperazine, piperidine and oxadiazole.

In a further embodiment each $R^1$ is independently selected from the group comprising amino, hydrogen, halogen, hydroxy, formyl, carboxy, cyano, nitro, $C_{1-8}$ alkyl, $C_{1-8}$ alkoxy, $C_{1-8}$ alkylthio, $C_{1-8}$ alkylsulphinyl, $C_{1-8}$ alkylsulphonyl, $C_{1-4}$ alkylamino, $C_{1-4}$ dialkylamino, benzyloxy, hydroxy-$C_{1-4}$ alkyl, hydroxy-$C_{1-4}$ alkanoyl-($C_{1-4}$ alkyl)-amino.

In an embodiment $R^2$ is hydrogen, $C_{1-4}$ alkyl, $C_{1-4}$ alkoxy or halogen, preferably methyl or hydrogen, more preferably hydrogen.

In a further embodiment $R^4$ is hydrogen, hydroxy, halogen, $C_{1-4}$ alkyl, $C_{1-4}$ alkoxy, di-[$C_{1-4}$ alkyl]amino, nitro or trifluoromethyl, preferably hydrogen, halogen or methyl, more preferably hydrogen.

In a preferred embodiment $R^7$ is an optionally substituted phenyl, dioxolanyl, thienyl, cyclohexyl or pyridyl group.

In a further embodiment, Z is absent or represents oxygen, $CH_2$, $NR^b$, $NR^b(CH_2)$, $(CH_2)NR^b$, $CH(CH_3)$, $O(CH_2)$, $(CH)CN$, $O(CF_2)$, $(CH_2)O$, $(CF_2)O$, $S(CH_2)$, $S(O)_m$, carbonyl or dicarbonyl, wherein $R^b$ is hydrogen or $C_{1-4}$ alkyl.

In a preferred embodiment Z is oxygen, dicarbonyl, $OCH_2$, $CH_2(CN)$, $S(O)m$ or $NR^b$, wherein $R^b$ is hydrogen or $C_{1-4}$ alkyl.

In a further prefered embodiment $R^6$ is benzyl,, halo-, dihalo- and trihalobenzyl, α-methylbenzyl, phenyl, halo, dihalo- and trihalophenyl, pyridyl, pyridylmethyl, pyridyloxy, pyridylmethoxy, thienylmethoxy, dioxolanylmethoxy, cyclohexylmethoxy, phenoxy, halo-, dihalo- and trihalophenoxy, phenylthio, benzyloxy, halo-, dihalo- and trihalobenzyloxy, $C_{1-4}$ alkoxybenzyloxy, phenyloxalyl or benzenesulphonyl, more preferably benzyl, fluorobenzyl, benzyloxy, fluorobenzyloxy, pyridylmethyl, phenyl, benzenesulphonyl, phenoxy or fluorophenoxy.

In a further embodiment $R^6$ is in the para position with respect to Y.

When the group Z is absent, $R^6=R^7$.

In a further embodiment A represents

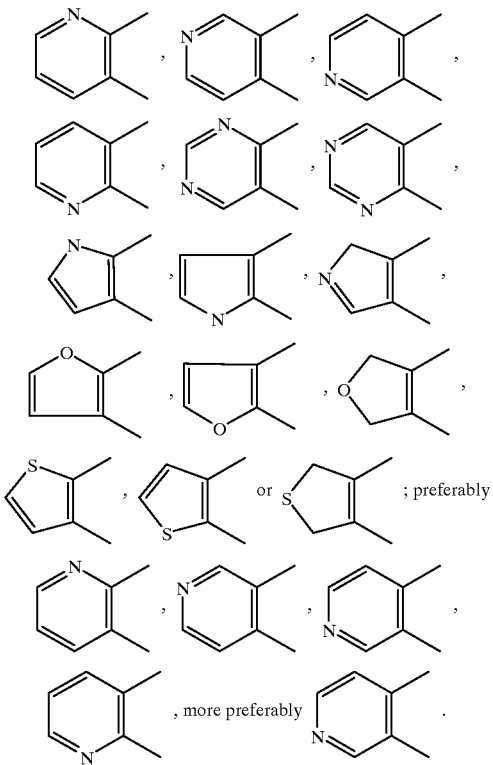

One or both of the rings comprising the mono or bicyclic ring system U may be aromatic or non-aromatic. The $R^4$ and $R^6$ groups may be bound to the ring system by either a carbon atom or a heteroatom of the ring system. The ring system itself may be bound to the bridging group by a carbon atom or a heteroatom. The $R^4$ and $R^6$ groups may be bound to either ring when U represents a bicyclic ring system, but these groups are preferably bound to the ring which is not bound to the bridging group Y in such a case.

Examples of suitable mono or bicyclic groups U include: isoindenyl, indenyl, indanyl, naphthyl, 1,2-dihydronaphthyl or 1,2,3,4-tetrahydronaphthyl, pyrrolyl, pyridinyl, pyridazinyl, pyrimidinyl, pyrazinyl, furanyl, 2H-pyranyl, thiophenyl, 1H-azepinyl, oxepinyl, thiepinyl, azocinyl, 2H-oxocinyl, thieno[2,3-b] furanyl, thianaphthenyl, indolyl, indolinyl, isoindolyl, isoindolinyl, indolizinyl, 1H-benzimidazolyl, 2,3-dihydro-1H-benzimidazolyl, 1H-indazolyl, 2,3-dihydro-1H-indazolyl, benzoxazolyl, 2,3-dihydrobenzoxazolyl, benzo[c]isoxazolyl, benzo[d] isoxazolyl, 2,3-dihydrobenzo[d]isoxazolyl, benzothiazoyl, 2,3-dihydrobenzothiazolyl, benzo[c]isothiazolyl, benzo[d] isothiazolyl, 2,3-dihydrobenzo[d]isothiazolyl, 1H-benzotriazolyl, benzo[c]furanyl, benzo[c][1,2,3] thiadiazolyl, benzo[d][1,2,3]oxadiazolyl, benzo[d][1,2,3] thiadiazolyl, quinolyl, 1,2-dihydroquinolinyl, 1,2,3,4-tetrahydroquinolinyl, isoquinolyl 1,2,3,4-tetrahydroisoquinolinyl, cinnolinyl, quinazolinyl, quinoxalinyl, phthalazinyl, 4H-1,4-benzoxazinyl, 2,3-dihydro-4H-1,4-benzoxazinyl, 4H-1,4-benzothiazinyl or 2,3-dihydro-4H-1,4-benzothiazinyl.

Suitably U represents an indolyl, isoindolyl, indolinyl, isoindolinyl, 1H-indazolyl, 2,3-dihydro-1H-indazolyl, 1H-benzimidazolyl, 2,3-dihydro-1H-benzimidazolyl or 1H-benzotriazolyl group.

In an embodiment, the optional substituents for the carbocyclic or heterocyclic moiety, which may be present at any available position of said moiety, are selected from the group comprising:

$(CH_2)_qS(O)_m$—$C_{1-4}$alkyl, $(CH_2)_qS(O)_m$—$C_{3-6}$cycloalkyl, $(CH_2)_qSO_2NR^8R^9$, $(CH_2)_qNR^8R^9$, $(CH_2)_qCO_2R^8$, $(CH_2)_qOR^8$, $(CH_2)_qCONR^8R^9$, $(CH_2)_qNR^8COR^9$, $(CH_2)_qCOR^8$, $(CH_2)_qR^8$, $NR^8SO_2R^9$ and $S(O)_mR^8$.

wherein q is an integer from 0 to 4 inclusive; m is 0, 1 or 2;

$R^8$ and $R^9$ are independently selected from the group comprising hydrogen, $C_{1-4}$ alkyl, $C_{3-6}$ cycloalkyl, aryl, a 5- or 6-membered saturated or unsaturated heterocyclic ring which may be the same or different and which contains one or more heteroatoms which are selected from N, O or $S(O)_m$, with the proviso that the heterocyclic ring does not contain two adjacent O or $S(O)_m$ atoms.

In a further embodiment the optional substituents for the carbocyclic or heterocyclic moiety are selected from the group comprising morpholine, piperazine, piperidine, pyrrolidine, tetrahydrofuran, dioxolane, oxothiolane and oxides thereof, dithiolane and oxides thereof, dioxane, pyridine, pyrimidine, pyrazine, pyridazine, furan, thiofuran, pyrrole, triazine, imidazole, trizole, tetrazole, pyrazole, oxazole, oxadiazole and thiadiazole.

Other optional substituents for the carbocyclic or heterocyclic moiety and also for other optionally substituted groups include, but are not limited to, hydroxy, halogen, trifluoromethyl, trifluoromethoxy, nitro, amino, cyano, $C_{1-4}$ alkoxy, $C_{1-4}$ alkylthio, $C_{1-4}$ alkyl carbonyl, carboxylate and $C_{1-4}$ alkoxy carboxyl.

In a further embodiment X represents N; A represents a pyridine ring; p is 0; n is 1; and the group R" is in the 6-position of the pyridopyrimidine ring system.

In a further embodiment X represents N; A represents a pyridine ring; n is 0; p is 1; and the group $R^1$ is in the 6-position of the pyridopyridimidine ring system.

In a preferred embodiment of the present invention there is provided a compound of formula (I) or a salt or solvate thereof wherein X represents N; Y represents $NR^a$, wherein $R^a$ is hydrogen or $C_{1-4}$ alkyl; A represents a pyridine ring; R" represents furan, thiophene, pyrrole, pyridine, pyrimidine, pyrazine, imidazole, oxazole, isoxazole, oxadiazole, tetrazole, triazole, dioxolane or a partially or fully hydrogenated derivative of any of these groups, optionally substituted by one or more $R^1$ groups selected from halo, $C_{1-4}$ alkyl, carboxy, formyl, hydroxy-$C_{1-4}$ alkyl, 1,3-dioxolan-2-yl, amino, $C_{1-4}$ alkylamino, di($C_{1-4}$ alkyl)amino, hydroxy-$C_{1-4}$ alkanoyl($C_{1-4}$ alkyl)amino, $C_{1-4}$ alkylamino-$C_{1-4}$ alkyl or di($C_{1-4}$ alkyl)amino-$C_{1-4}$ alkyl; p is 0; $R^2$ represents hydrogen; $R^4$ represents hydrogen or methyl; U represents indolyl, benzimidazolyl or indazolyl, more preferably indazolyl; and $R^6$ represents phenyl, benzyl, α-methylbenzyl, fluorobenzyl, benzenesulphonyl, phenoxy, fluorophenoxy, benzyloxy or fluorobenzyloxy.

In a further preferred embodiment of the present invention there is provided a compound of formula (I) or a salt or solvate thereof wherein X represents N; Y represents $NR^a$, wherein $R^a$ is hydrogen or $C_{1-4}$ alkyl; A represents a pyridine ring, R" represents furan, thiophene, pyrrole, pyridine, pyrimidine, pyrazine, imidazole, oxazole, isoxazole, oxadiazole, tetrazole, triazole, dioxolane or a partially or fully hydrogenated derivative of any of these groups, optionally substituted with an $R^1$ group selected from methylsulphonylethylaminomethyl, methylsulphonylethylamino-carbonyl, methylsulphinylethylamino-methyl, methylsulphinylethylamino-carbonyl, methylsulphonylpropylamino-methyl, methylsulphinylpropylamino-methyl, methylsulphonylpropyamino-carbonyl, methylsulphinylpropylamino-carbonyl, methylsulphonylethyl-(methylamino)-methyl, methylsulphonylethyl-(methylamino)-carbonyl, methylsulphinylethyl-(methylamino)-methyl, methylsulphinylethyl-(methylamino)-carbonyl, methylsulphonylpropyl-(methylamino)-methyl, methylsulphinylpropyl-(methylamino)-methyl, methylsulphonylpropyl-(methylamino)-carbonyl, methylsulphinylpropyl-(methylamino)-carbonyl, methylsulphonamidoethylamino-methyl, methylsulphonamidopropylamino-methyl, sarcosinamidomethyl, glycinylmethyl, glycinamidomethyl, glycinylmethyl methyl ester, acetylaminoethylaminomethyl, piperazinylmethyl, methylpiperazinylmethyl, piperidinylmethyl, N-(prolinamido)methyl, (N,N-dimethylprolinamido)methyl, pyridylaminomethyl, cyclopropylaminomethyl, N-(piperidin-4-yl)-N-methylaminomethyl, N,N-dimethylaminoprop-2-ylaminomethyl, N-(2-dimethylaminoethyl)-N-ethylaminomethyl, isopropylacetamido, N-morpholinylacetamido or tetrahydrofuranomethylaminomethyl and optionally further substituted by one or more $C_{1-4}$ alkyl groups; p is 0; $R^2$ represents hydrogen; $R^4$ represents hydrogen or methyl; U represents indolyl, benzimidazolyl or indazolyl, more preferably indazolyl; and $R^6$ represents phenyl, benzyl, α-methylbenzyl, fluorobenzyl, benzenesulphonyl, phenoxy, fluorophenoxy, benzyloxy or fluorobenzyloxy.

In a further preferred embodiment of the present invention there is provided a compound of formula (I) or a salt or solvate thereof, wherein X represents N; Y represents $NR^a$ wherein $R^a$ is hydrogen or $C_{1-4}$ alkyl; A represents a pyridine ring; n is 0; each $R^1$ group is selected from hydrogen, halo, $C_{1-4}$ alkyl, carboxy, formyl, hydroxy-$C_{1-4}$ alkyl, 1,3-dioxolan-2-yl, benzyloxy, amino, $C_{1-4}$ alkylamino, di($C_{1-4}$ alkyl)amino, hydroxy-$C_{1-4}$ alkanoyl($C_{1-4}$ alkyl)amino, $C_{1-4}$ alkylamino-$C_{1-4}$ alkyl, di($C_{1-4}$ alkyl)amino-$C_{1-4}$ alkyl, methylsulphonylethylaminomethyl, methylsulphonylethylamino-carbonyl, methylsulphinylethylamino-methyl, methylsulphinylethylamino-carbonyl, methylsulphonylpropylamino-methyl, methylsulphinylpropylamino-methyl, methylsulphonylpropyamino-carbonyl, methylsulphinylpropylamino-carbonyl, methylsulphonylethyl-(methylamino)-methyl, methylsulphonylethyl-(methylamino)-carbonyl, methylsulphinylethyl-(methylamino)-methyl, methylsulphinylethyl-(methylamino)-carbonyl, methylsulphonylpropyl-(methylamino)-methyl, methylsulphinylpropyl-(methylamino)-methyl, methylsulphonylpropyl-(methylamino)-carbonyl, methylsulphinylpropyl-(methylamino)-carbonyl, methylsulphonamidoethylamino-methyl, methylsulphonamidopropylamino-methyl, sarcosinamidomethyl, glycinylmethyl, glycinamidomethyl, glycinylmethyl methyl ester, acetylaminoethylaminomethyl, piperazinylmethyl, methylpiperazinylmethyl, piperidinylmethyl, N-(prolinamido)methyl, (N,N-dimethylprolinmido)methyl, pyridylaminomethyl, cyclopropylaminomethyl, N-(piperidin-4-yl)-N-methylaminomethyl, N,N-dimethylaminoprop-2-ylaminomethyl, N-(2-dimethylaminoethyl)-N-ethylaminomethyl, isopropylacetamido, N-morpholinylacetamido or tetrahydrofuranomethylaminomethyl; $R^2$ represents hydrogen; $R^4$ represents hydrogen or methyl; U represents indolyl, benzimidazolyl or indazolyl, more preferably indazolyl; and $R^6$ represents phenyl, benzyl, α-methylbenzyl, fluorobenzyl, benzenesulphonyl, phenoxy, fluorophenoxy, benzyloxy or fluorobenzyloxy.

In an especially prefered embodiment of the present invention there is provided a compound of formula (I) or a salt or solvate thereof wherein X represents N; Y represents $NR^a$, wherein $R^a$ is hydrogen or $C_{1-4}$ alkyl; A represents a pyridine ring; R" represents a furan, imidazole, triazole, oxadiazole, pyrrolidine, piperidine or piperazine ring, optionally substituted by one or more $R^1$ groups selected from 1,3-dioxolan-2-yl, formyl, carboxy, $C_{1-4}$-alkyl, prolinamidomethyl, isopropylacetamido, N-morpholinylacetamido, methylsulphonylethylaminomethyl or methylsulphonylethylaminocarbonyl; p is 0; $R^2$ represents hydrogen; $R^4$ represents hydrogen or methyl; U represents indazolyl, indolyl or benzimidazolyl, more preferably indazolyl; and $R^6$ represents benzyl, fluorobenzyl, pyridylmethyl or benzenesulphonyl.

In a further especially preferred embodiment of the present invention there is provided a compound of formula (I) or a salt or solvate thereof wherein X represents N; Y represents $NR^a$, wherein $R^a$ is hydrogen or $C_{1-4}$ alkyl; A represents a pyridine ring; n is 0; each $R^1$ group is selected from hydrogen, halo, benzyloxy, amino, $C_{1-4}$ alkylamino, di($C_{1-4}$ alkyl)amino or hydroxy-$C_{1-4}$ alkanoyl($C_{1-4}$ alkyl) amino, more preferably dimethylamino; $R^2$ represents hydrogen; $R^4$ represents hydrogen or methyl; U represents indazolyl, indolyl or benzimidazolyl, more preferably indazolyl; and $R^6$ represents benzyl, fluorobenzyl, pyridylmethyl or benzenesulphonyl.

Preferred compounds of the present invention include:
(1-Benzyl-1H-indazol-5-yl)-(6-chloro-pyrido[3,4-d]pyrimidin-4-yl)-amine;
N4-(1-Benzyl-1H-indazol-5-yl)-N6,N6-dimethyl-pyrido[3,4-d]pyrimidine-4,6-diamine;
(1-Benzyl-1H-indazol-5-yl)-6-(N-(2-hydroxyethyl)-N-methylamino)-pyrido[3,4-d]pyrimidin-4-yl)-amine;
(1-Benzyl-1H-indazol-5-yl)-(pyrido[3,4-d]pyrimidin-4-yl)-amine;
(2-Benzyl-1H-indazol-5-yl)-(6-chloro-pyrido[3,4-d]pyrimidin-4-yl)-amine;
N4-(1-Benzyl-1H-indol-5-yl)-N6,N6-dimethyl-pyrido[3,4-d]pyrimidine-4,6-diamine;
N4-(2-Benzyl-1H-benzimidazol-5-yl)-N6,N6-dimethyl-pyrido[3,4-d]-pyrimidine-4,6-diamine;

(1-Benzyl-1H-indazol-5-yl)-(6-(5-[1,3-dioxolan-2-yl]-furan-2-yl)-pyrido[3,4-d]-pyrimidin-4-yl)-amine;

5-(4-(1-Benzyl-1H-indazol-5-ylamino)-pyrido[3,4-d]pyrimidin-6-yl)-furan-2-carbaldehyde;

(2S)-1-(5-(4-(1-Benzyl-1H-indazol-5-ylamino)-6-pyrido[3,4-d]pyrimidin-6-yl)-furan-2-ylmethyl)-pyrrolidin-2-carboxylic acid amide;

(1-Benzyl-1H-indazol-5-yl)-(6-(3-methyl-3H-imidazol-4-yl)-pyrido[3,4-d]pyrimidin-4-yl)-amine;

N6,N6-Dimethyl-N4-(1-pyridin-2-ylmethyl-1H-indazol-5-yl)-pyrido[3,4-d]pyrimidine-4,6-diamine;

N6,N6-Dimethyl-N4-(1-pyridin-3-ylmethyl-1H-indazol-5-yl)-pyrido[3,4-d]pyrimidine-4,6-diamine;

N4-(1-Benzyl-3-methyl-1H-indazol-5-yl)-N6,N6-dimethyl-pyrido[3,4-d]pyrimidine-4,6-diamine;

N4-(1-(2-Fluoro-benzyl)-1H-indazol-5-yl)-N6,N6-dimethyl-pyrido[3,4-d]pyrimidine-4,6-diamine;

N4-(1-(3-Fluoro-benzyl)-1H-indazol-5-yl)-N6,N6-dimethyl-pyrido[3,4-d]pyrimidine-4,6-diamine;

N4-(1-(4-Fluoro-benzyl)-1H-indazol-5-yl)-N6,N6-dimethyl-pyrido[3,4-d]pyrimidine-4,6-diamine;

N4-(1-Benzenesulphonyl-1H-indol-5-yl)-N6,N6-dimethyl-pyrido[3,4-d]pyrimidine-4,6-diamine;

N4-(3-Benzenesulphonyl-1H-indol-5-yl)-N6,N6-dimethyl-pyrido[3,4-d]pyrimidine-4,6-diamine;

(1-Benzyl-1H-indazol-5-yl)-(6-imidazol-1-yl-pyrido[3,4-d]pyrimidin-4-yl)-amine;

(1-Benzyl-1H-indazol-5-yl)-(6-(1,2,4-triazol-1-yl-pyrido[3,4-d]pyrimidin-4-yl)-amine;

(1-Benzyl-1H-indazol-5-yl)-(6-(1,2,3-triazol-2-yl-pyrido[3,4-d]pyrimidin-4-yl)-amine;

(1-Benzyl-1H-indazol-5-yl)-(6-(1,2,3-triazol-1-yl-pyrido[3,4-d]pyrimidin-4-yl)-amine;

(1-Benzyl-1H-indazol-5-yl)-(6-pyrrolidin-1-yl-pyrido[3,4-d]pyrimidin-4-yl)-amine;

(1-Benzyl-1H-indazol-5-yl)-(6-piperidin-1-yl)-pyrido[3,4-d]pyrimidin-4-yl)-amine;

N4-(1-Benzyl-1H-indazol-5-yl)-N6-ethyl-N6-methyl-pyrido[3,4-d]pyrimidine-4,6-diamine;

2-(4-(4-(1-Benzyl-1H-indazol-5-ylamino)-pyrido[3,4-d]pyrimidin-6-yl)-piperazin-1-yl)-N-isopropyl-acetamide;

2-(4-(4-(1-Benzyl-1H-indazol-5-ylamino)-pyrido[3,4-d]pyrimidin-6-yl)-piperazin-1-yl)-1-morpholin-4-yl-ethanone;

(1-Benzyl-1H-indazol-5-yl)-(6-(5-methyl-1,3,4-oxadiazol-2-yl)-pyrido[3,4-d]pyrimidin-4-yl)-amine;

(1-(3-Fluoro-benzyl)-1H-indazol-5-yl)-(6-(5-methyl-1,3,4-oxadiazol-2-yl)-pyrido[3,4-d]pyrimidin-4-yl)-amine;

(1-Benzyl-1H-indol-5-yl)-(6-chloro-pyrido[3,4-d]pyrimidin-4-yl)-amine;

(1-Benzyl-1H-indazol-5-yl)-(6-(4-methyl-piperazin-1-yl)-pyrido[3,4-d]pyrimidin-4-yl)-amine;

(1-Benzyl-1H-indazolyl-5-yl)-(6-benzyloxy-pyrido[3,4-d]pyrimidin-4-yl)-amine;

(1-Benzyl-1H-indazol-5-yl)-(6-(5-((2-methanesuphonyl-ethylamino)-methyl)-furan-2-yl)-pyrido-[3,4-d]pyrimidin-4-yl)-amine;

5-[4-(1-Benzyl-1H-indazol-5-ylamino)-pyrido-[3,4-d]pyrimidin-6-yl]-furan-2-carboxylic acid;

5-[4-(1-benzyl-1H-indazol-5-ylamino)-pyrido-[3,4-d]pyrimidin-6-yl]-furan-2-carboxylic acid 2-methanesulphonyl-ethylamide;

N4-(1-Benzyl-1H-indazol-5-yl)-N6-methyl-pyrido[3,4-d]pyrimidine-4,6-diamine; N4-[1-(4-Hydroxybenzyl)-1H-indazol-5-yl)-N6,N6-dimethyl-pyrido[3,4-d]pyrimidine-4,6-diamine;

and salts or solvates thereof, particularly pharmaceutically acceptable salts or solvates thereof.

Other preferred compounds of the present invention include:

N4-[1-(S,R-α-Methylbenzyl)-1H-indazol-5-yl]-N6,N6-dimethyl-pyrido-[3,4-d]pyrimidine-4,6-diamine;

N4-(3-Benzylsulphonyl-1H-indazol-6-yl)-N6,N6-dimethyl-pyrido[3,4-d]-pyrimidine-4,6-diamine;

N4-(3-Benzyl-1H-indazol-6-yl)-N6,N6-dimethyl-pyrido[3,4-d]-pyrimidine-4,6-diamine;

and salts or solvates thereof, particularly pharmaceutically acceptable salts or solvates thereof.

Particularly preferred compounds of the present invention include:

N4-(1-Benzyl-1H-indazol-5-yl)-N6,N6-dimethyl-pyrido[3,4-d]pyrimidine-4,6-diamine;

N4-(1-(3-Fluoro-benzyl)-1H-indazol-5-yl)-N6,N6-dimethyl-pyrido[3,4-d]pyrimidine-4,6-diamine;

N4-(1-Benzyl-1H-indazol-5-yl)-N6-ethyl-N6-methyl-pyrido[3,4-d]pyrimidine-4,6-diamine;

(1-Benzyl-1H-indazol-5-yl)-(6-(5-((2-methanesuphonyl-ethylamino)-methyl)-furan-2-yl)-pyrido-[3,4-d]pyrimidin-4-yl)-amine;

N4-(1-Benzyl-1H-indazol-5-yl)-N6-methyl-pyrido[3,4-d]pyrimidine-4,6-diamine;

and salts or solvates thereof, particularly pharmaceutically acceptable salts or solvates thereof.

Certain compounds of formula (I) may exist in steroisomeric forms (e.g. they may contain one or more asymmetric carbon atoms or may exhibit cis-trans isomerism). The individual steroisomers (enantiomers and diastereoisomers) and mixtures of these are included within the scope of the present invention. Likewise, it is understood that compounds of formula (I) may exist in ntautomeric forms other than that shown in the formula and these are also included within the scope of the present invention.

Salts of the compounds of the present invention may comprise acid addition salts derived from a nitrogen in the compound of formula (I). The therapeutic activity resides in the moiety derived from the compound of the invention as defined herein and the identity of the other component is of less importance although for therapeutic and prophylactic purposes it is, preferably, pharmaceutically acceptable to the patient. Examples of pharmaceutically acceptable acid addition salts include those derived from mineral acids, such as hydrochloric, hydrobromic, phosphoric, metaphosphoric, nitric and sulphuric acids, and organic acids, such as tartaric, acetic, trifluoracetic, citric, malic, lactic, fumaric, benzoic, glycolic, gluconic, succinic and methanesulphonic and arylsulphonic, for example p-toluenesulphonic, acids.

According to a further aspect of the present invention there is provided a process for the preparation of a compound of formula (I) as defined above which comprises the steps:

(a) the reaction of a compound of formula (II)

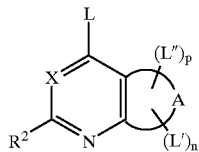
(II)

wherein A, X, n, p and $R^2$ are as defined above and L, L' and L" are suitable leaving groups, with a compound of formula (III)

UYH (III)

wherein U and Y are as defined above, to prepare a compound of formula (IV)

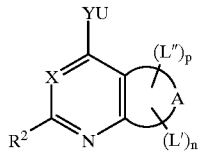
(IV)

and subsequently (b) where n is 1, reaction with an appropriate reagent to substitute the group R" onto the ring A by replacement of the leaving group L'; and (c) where p is other than 0, reaction with appropriate reagent(s) to substitute the group(s) $R^1$ onto the ring A by replacement of the leaving group(s) L"; and, if desired, (d) subsequently converting the compound of formula (I) thereby obtained into another compound of formula (I) by means of appropriate reagents.

Alternatively, the compound of formula (II) as defined above is reacted with the appropriate reagents to substitute the groups R" and $R^1$ onto the ring A by replacement of the respective leaving groups and then the product thereby obtained (of formula (V) below) is reacted with the compound of formula (III) as defined above, followed, if desired, by conversion of the compound of formula (I) thereby obtained into another compound of formula (I).

In a variant of this alternative the compound of formula (V)

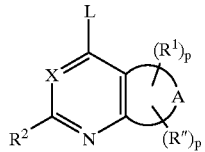
(V)

may be prepared by the reaction of a compound of formula (VI)

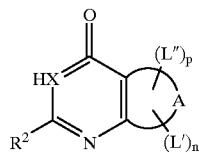
(VI)

with appropriate reagents to substitute the group(s) $R^1$ and the group R" onto the ring A to prepare a compound of formula (VII)

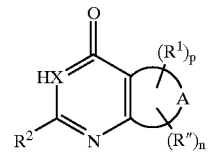
(VII)

and subsequent reaction to incorporate the leaving group L. For example, a chloro leaving group can be incorporated by reaction of a corresponding 3,4-dihydropyrimidone with carbon tetrachloride/triphenylphosphine in an appropriate solvent.

Simplified versions of these general processes will apply where either (i) p is 0 and n is 1 or (ii) where n is 0 and p is other than 0.

The group R" may, therefore, be substituted onto the ring A by replacement of a suitable leaving group. This is especially suitable for preparing compounds where R" is a substituted or unsubstituted phenyl or heterocyclic ring system; such compounds may, for example, be prepared by reaction of the corresponding aryl or heteroaryl stannane derivative with the corresponding compound of formula (IV) carrying the leaving group L' in the appropriate position on the ring.

The group(s) $R^1$ may, therefore, also be substituted onto the ring A by replacement of suitable leaving group(s). This is especially suitable for preparing compounds of formula (I) wherein an $R^1$ group is linked to the ring A by a nitrogen atom; such compounds may, for example, be obtained by reaction of the amine corresponding to the group $R^1$ with the corresponding compound carrying a halo substituent in the appropriate position on the ring A.

The reagents used to effect the substitution of the groups R" and $R^1$ onto the ring A may, in certain circumstances, include appropriate protecting group(s) well known to the person skilled in the art for particular functionalities. This may, for example, be suitable where either of the groups R" or $R^1$ contain a free amino functionality. Such protecting group(s) would be removed by standard methods after the substitution onto the ring A has been effected. For a description of protecting groups and their use see T. W. Greene and P. G. M. Wuts, "Protective Groups in Organic Synthesis", 2nd edn., John Wiley & Sons, New York, 1991.

According to a further aspect of the present invention there is provided a process for the preparation of a compound of formula (I) as defined above which comprises the steps:

(a) reacting a compound of formula (IV) as defined above with appropriate reagent(s) to prepare a compound wherein either the group L' (when n=1) or the group(s) L" (when p is other than 0) is(are) replaced with an appropriately functionalised group Z;

and (b) subsequently converting the group Z into the group R" where L' has been replaced or into the group $R^1$ where L" has been replaced by means of appropriate reagent(s);

(c) reacting with appropriate reagents to substitute the other of $R^1$ and R" onto the ring A by replacement of the remaining leaving group L" and L' respectively, if present;

and, if desired, (d) subsequently converting the compound of formula (I) thereby obtained into another compound of formula (I) by means of appropriate reagents.

Such processes are particularly suitable for the preparation of compounds of formula (I) wherein either r" carries or $R^1$ represents a substituent selected from $M^1$-$M^2$-$M^3$-$M^4$, $M^1$-$M^5$ or $M^1$-$M^2$-$M^{3'}$-$M^6$ as defined above in which $M^2$ represents $NR^{12}$. In such cases preferably the group Z carries a terminal formyl group (CHO).

Such processes are especially suitable for the preparation of compounds of formula (I) wherein either (i) p is 0, n is 1 and R" carries a substituent selected from $M^1$-$M^2$-$M^3$-$M^4$, $M^1$-$M^5$ or $M^1$-$M^2$-$M^{3'}$-$M^6$ as defined above in which $M^2$ represents $NR^{12}$, or (ii) p is 1, n is 0 and $R^1$ is selected from $M^1$-$M^2$-$M^3$-$M^4$, $M^1$-$M^5$ or $M^1$-$M^2$-$M^{3'}$-$M^6$ as defined above in which $M^2$ represents $NR^{12}$.

Where Z carries a formyl group the compound may be suitably prepared from the corresponding dioxolanyl substituted compound, for example by acid hydrolysis. The dioxolanyl substituted compound may be prepared by reaction of a compound of formula (IV) with an appropriate reagent to substitute the relevant leaving group with the substituent carrying the dioxolanyl ring. This reagent could, for example, be an appropriate heteroaryl stannane derivative.

Where Z carries a terminal formyl group the compound could suitably be prepared by reaction of a compound of formula (IV) with an appropriate heteroaryl stannane derivative. This derivative is either readily available or can be readily synthesised by those skilled in the art using conventional methods of organic synthesis. Suitable possibilities for preparation of compounds where R" carries the aforementioned substituents include the following schematic examples:

Therefore a suitable process may comprise reaction of the compound in which the group Z carries a terminal formyl group (i.e. a —CHO or —($C_{1-3}$ alkylene)—CHO group) with a compound of formula $HM^2$-$M^3$-$M^4$, a compound of formula $HM^2$-$M^{3'}$-$M^6$ or a compound of formula $HM^5$, wherein $M^2$ represents $NR^{12}$. The reaction preferably involves a reductive amination by means of an appropriate reducing agent, for example sodium triacetoxyborohydride.

A similar process would be involved where in $M^1$ one $CH_2$ group was replaced with a CO group and $M^2$ was $NR^{12}$. If necessary, in certain circumstances, the ketone could be protected by standard methods to ensure that the reductive amination involved the aldehyde functionality.

For the preparation of those compounds wherein in $M^1$ one $CH_2$ group adjacent to $M^2$ is replaced with a CO group a suitable process would comprise reaction of a compound in which the group Z carries a —($C_{0-3}$ alkylene)—$CO_2H$ group with a compound of formula $HM^2$-$M^3$-$M^4$, a compound of formula $HM^2$-$M^{3'}$-$M^6$ or a compound of formula $HM^5$, wherein $M^2$ represents $NR^{12}$.

Alternatively, an analogous scheme to those described above could be used wherein the substitution of groups R" and $R^1$ onto the ring A occurs prior to the coupling reaction with the compound of formula (III).

According to a further alternative process the group Z is converted into the group R" by a de novo synthesis of a substituted or unsubstituted heterocyclic ring system using appropriate reagents. Such a process would involve standard synthetic methodology known to the person skilled in the art for building up the heterocyclic ring system.

For example, Z could suitably represent an alkyne group which when reacted with an appropriate nitrile oxide results

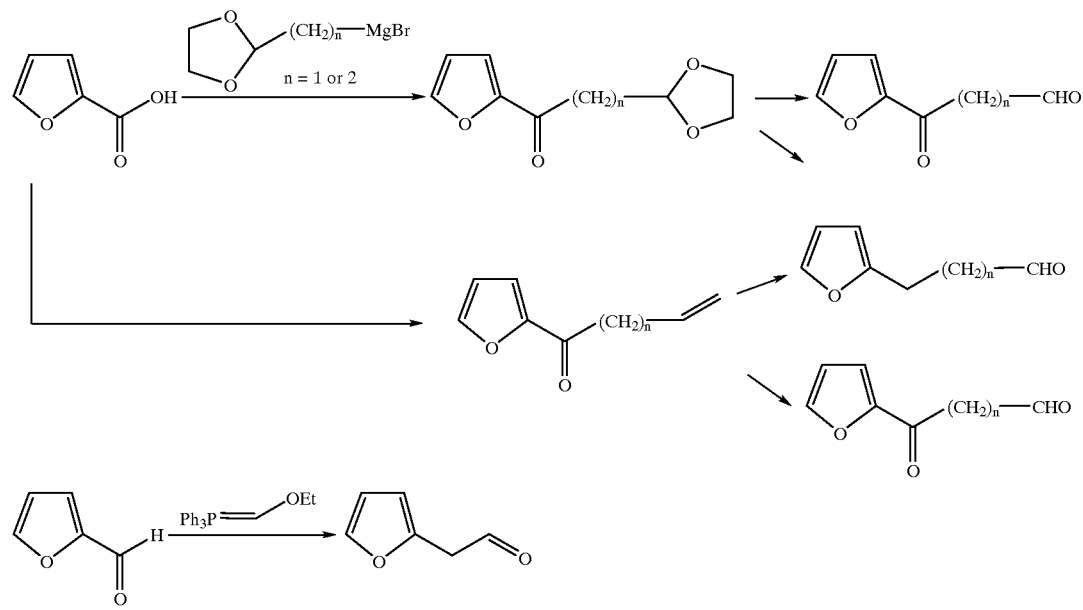

The resulting compounds would, for example, then be converted into the respective stannane derivative.

Analogous methods could be used for phenyl and other heterocyclic ring systems and also for the preparation of compounds where $R^1$ represents one of the aforementioned substituents.

in the formation of an isoxazole ring system; reaction with an azide would result in the formation of a triazole ring system. The group Z could also suitably represent an amidoxime group (derived from a cyano group) which when reacted with an activated carboxylic acid derivative (such as an acid chloride or an acid imidazolide) would result in the formation of a 1,2,4-oxadiazole ring system. The group Z could also suitably represent a bromomethylenecarbonyl group which would be reacted with an imidate to result in the formation of an oxazole ring system, with a guanidino group to result in the formation of an N-imidazole ring system or with an amidine group to result in the formation of a C-imidazole ring system. The group Z could also suitably represent an activated carboxylic acid group which would be reacted to form a hydrazinoketone which would subsequently be reacted with another activated carboxylic acid derivative to result in the preparation of a 1,3,4-oxadiazole ring system. Thus reaction of a compound carrying a relevant Z group with appropriate reagents carrying one of —C=N=O, —NH—C(NH$_2$)=NH, —COX, —C(NH$_2$)=NOH, —C(OMe)=NH, or —C(NH$_2$)=NH as a terminal group would result in the formation of the ring systems indicated above.

Alternatively, an analogous scheme to those described above could be used wherein the substitution of the group R" onto the ring A occurs prior to the coupling reaction with the compound of formula (III).

The following scheme outlines, for example, the synthesis of derivatives carrying a substituted 1,3,4-oxadiazole ring as an R" substituent:

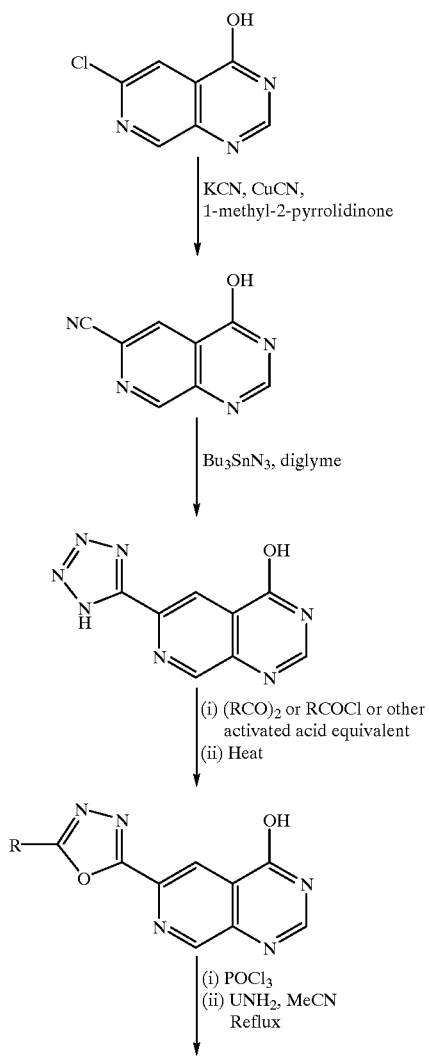

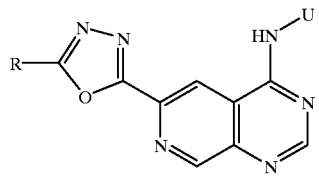

Such processes are particularly suitable for the preparation of the compounds of formula (I) wherein R" carries a substituent selected from $M^1$-$M^2$-$M^3$-$M^4$, $M^1$-$M^5$ or $M^1$-$M^2$-$M^{3'}$-$M^6$ as defined above in which $M^2$ represents $CR^{12}R^{13}$, including those in which in $M^1$ one $CH_2$ group is replaced by a CO group.

Such processes are especially suitable for the preparation of compounds of formula (I) wherein either (i) p is 0, n is 1 and R" carries a substituent selected from $M^1$-$M^2$-$M^3$-$M^4$, $M^1$-$M^5$ or $M^1$-$M^2$-$M^{3'}$-$M^6$ as defined above in which $M^2$ represents $CR^{12}R^{13}$, or (ii) p is 1, n is 0 and $R^1$ is selected from $M^1$-$M^2$-$M^3$-$M^4$, $M^1$-$M^5$ or $M^1$-$M^2$-$M^{3'}$-$M^6$ as defined above in which $M^2$ represents $CR^{12}R^{13}$.

Suitable leaving groups for L, L' and L" will be well known to those skilled in the art and include, for example, halo such as chloro and bromo; sulphonyloxy groups such as methanesulphonyloxy and toluene-p-sulphonyloxy; alkoxy groups; and triflate.

The coupling reaction referred to above with the compound of formula (III) is conveniently carried out in the presence of a suitable inert solvent, for example a $C_{1-4}$ alkanol, such as isopropanol, a halogenated hydrocarbon, and ether, an aromatic hydrocarbon or a dipolar aprotic solvent such as acetone or acetonitrile at a non-extreme temperature, for example from 0 to 150°, suitably 10 to 100° C., preferably 50 to 100° C.

Optionally, the reaction is carried out in the presence of a base when Y=NH. Examples of suitable bases include an organic amine such as triethylamine, or an alkaline earth metal carbonate, hydride, or hydroxide, such as sodium or potassium carbonate, hydride or hydroxide. When YH=OH or SH it is necessary to perform the reaction in the presence of a base, and in such a case the product is not obtained as the salt.

The compound of formula (I) in the case in which Y=$NR^b$ may be obtained from this process in the form of a salt with the acid HL, wherein L is as hereinbefore defined, or as the free base by treating the salt with a base as hereinbefore defined.

The compounds of formulae (II) and (III) as defined above, the reagents to substitute the group(s) $R^1$ and the group R", and the reagent(s) to convert the group Z into the group $R^1$ or R" are either readily available or can be readily synthesised by those skilled in the art using conventional methods of organic synthesis.

As indicated above, the compound of formula (I) prepared may be converted to another compound of formula (I) by chemical transformation of the appropriate substituent or substituents using appropriate chemical methods (see for example, J. March "Advanced Organic Chemistry", Edition III, Wiley Interscience, 1985).

For example, a group $R^1$ may be substituted onto the ring A by replacement of another group $R^1$ which is a suitable leaving group. This is especially suitable for preparing compounds of formula (I) wherein an $R^1$ group is linked to the ring A by a nitrogen atom; such compounds may, for example, be obtained by reaction of the amine corresponding to the group $R^1$ with the corresponding compound of formula (I) carrying a halo substituent in the appropriate position on the ring A.

Similarly a group R" may be substituted onto the ring A by replacement of a group $R^1$ which is a suitable leaving group. This is especially suitable for preparing compounds where R" is a phenyl or heterocyclic ring system; such compounds may, for example, be prepared by reaction of the corresponding aryl or heteroaryl stannane derivative with the corresponding compound of formula (I) carrying a halo substituent in the appropriate position on the ring A.

For example, a compound containing an alkyl or aryl mercapto group may be oxidised to the corresponding sulphinyl or sulphonyl compound by use of an organic peroxide (e.g. benzoyl peroxide) or suitable inorganic oxidant (eg OXONE®).

A compound containing a nitro substituent may be reduced to the corresponding amino-compound, e.g. by use of hydrogen and an appropriate catalyst (if there are no other susceptible groups) or by use of Raney Nickel and hydrazine hydrate.

Amino or hydroxy substituents may be acylated by use of an acid chloride or an anhydride under appropriate conditions. Equally an acetate or amide group may be cleaved to the hydroxy or amino compound respectively by treatment with, for example, dilute aqueous base.

In addition reaction of an amino substituent with triphosgene and another amine (eg aqueous ammonia, dimethylamine) gives the urea substituted product.

An amino substituent may also be converted to a dimethylamino substituent by reaction with formic acid and sodium cyanoborohydride.

A formyl substituent may be converted to a hydroxymethyl or a carboxy substituent by standard reduction or oxidation methods respectively.

All of the above-mentioned chemical transformations may also be used to convert one compound of formula (II) to a further compound of formula (II) prior to any subsequent reaction; or to convert one compound of formula (II) to a further compound of formula (III) prior to any subsequent reaction.

Various intermediate compounds used in the above-mentioned processes, including but not limited to certain of the compounds of formulae (II), (III), (IV), (V), (VI) and (VII) as illustrated above, are novel and thus represent a further aspect of the present invention.

The compounds of formula (I) and salts thereof have anticancer activity as demonstrated hereinafter by their inhibition of the protein tyrosine kinase c-erbB-2, c-erbB-4 and/or EGF-r enzymes and their effect on selected cell lines whose growth is dependent on c-erbB-2 or EGF-r tyrosine kinase activity.

The present invention thus also provides compounds of formula (I) and pharmaceutically acceptable salts or solvates thereof for use in medical therapy, and particularly in the treatment of disorders mediated by aberrant protein tyrosine kinase activity such as human malignancies and the other disorders mentioned above. The compounds of the present invention are especially useful for the treatment of disorders caused by aberrant c-erbB-2 and/or EGF-r activity such as breast, ovarian, gastric, pancreatic, non-small cell lung, bladder, head and neck cancers, and psoriasis.

A further aspect of the invention provides a method of treatment of a human or animal subject suffering from a disorder mediated by aberrant protein tyrosine kinase activity, including susceptible malignancies, which comprises administering to said subject an effective amount of a compound of formula (I) or a pharmaceutically acceptable salt or solvate thereof.

A further aspect of the present invention provides the use of a compound of formula (I), or a pharmaceutically acceptable salt or solvate thereof, in therapy.

A further aspect of the present invention provides the use of a compound of formula (I), or a pharmaceutically acceptable salt or solvate thereof, in the preparation of a medicament for the treatment of cancer and malignant tumours.

A further aspect of the present invention provides the use of a compound of formula (I), or a pharmaceutically acceptable salt or solvate thereof, in the preparation of a medicament for the treatment of psoriasis.

Whilst it is possible for the compounds, salts or solvates of the present invention to be administered as the new chemical, it is preferred to present them in the form of a pharmaceutical formulation.

According to a further feature of the present invention there is provided a pharmaceutical formulation comprising at least one compound of formula (I), or a pharmaceutically acceptable salt or solvate thereof, together with one or more pharmaceutically acceptable carriers, diluents or excipients.

Pharmaceutical formulations may be presented in unit dose forms containing a predetermined amount of active ingredient per unit dose. Such a unit may contain for example 0.5 mg to 1 g, preferably 70 mg to 700 mg, more preferably 5 mg to 100 mg of a compound of the formula (I) depending on the condition being treated, the route of administration and the age, weight and condition of the patient.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318(1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists which may be generated by means of various types of metered dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Preferred unit dosage formulations are those containing a daily dose or sub-dose, as herein above recited, or an appropriate fraction thereof, of an active ingredient.

It should be understood that in addition to the ingredients particularly mentioned above, the formulations may include other agents conventional in the art having regard to the type of formulation in question, for example those suitable for oral administration may include flavouring agents.

The animal requiring treatment with a compound, salt or solvate of the present invention is usually a mammal, such as a human being.

A therapeutically effective amount of a compound, salt or solvate of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of the present invention for the treatment of neoplastic growth, for example colon or breast carcinoma will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. An effective amount of a salt or solvate of the present invention may be determined as a proportion of the effective amount of the compound per se.

The compounds of the present invention and their salts and solvates may be employed alone or in combination with other therapeutic agents for the treatment of the above-mentioned conditions. In particular, in anti-cancer therapy, combination with other chemotherapeutic, hormonal or antibody agents is envisaged. Combination therapies according to the present invention thus comprise the administration of at least one compound of formula (I) or a pharmaceutically acceptable salt or solvate thereof and at least one other pharmaceutically active agent. The compound(s) of formula (I) and the other pharmaceutically active agent(s) may be administered together or separately and, when administered separately this may occur simultaneously or sequentially in any order. The amounts of the compound(s) of formula (I) and the other pharmaceutically active agent(s) and the relative timings of administration will be selected in order to achieve the desired combined therapeutic effect.

Certain embodiments of the present invention will now be illustrated by way of example only. The physical data given for the compounds exemplified is consistent with the assigned structure of those compounds.

$^1$H NMR spectra were obtained at 500 MHz on a Bruker AMX500 spectrophotometer, on a Bruker spectrophotometer at 300 Mz, or on a Bruker AC250 or Bruker AM250 spectrophotometer at 250 MHz. J values are given in Hz. Mass spectra were obtained on one of the following machines; VG Micromass Platform (electrospray positive or negative), HP5989A Engine (thermospray positive) or Finnigan-MAT LCQ (ion trap) mass spectrometer. Analytical thin layer chromatography (tlc) was used to verify the purity of some intermediates which could not be isolated or which were too unstable for full characterisation, and to follow the progess of reactions. Unless otherwise stated, this was done using silica gel (Merck Silica Gel 60 F254). Unless otherwise stated, column chromatography for the purification of some compounds used Merck Silica gel 60 (Art. 1.09385, 230–400 mesh), and the stated solvent system under pressure.

Petrol refers to petroleum ether, either the fraction boiling at 40–60° C., or at 60–80° C.

Ether refers to diethylether.

DMAP refers to 4-dimethylaminopyridine.

DMF refers to dimethylformamide.

DMSO refers to dimethylsulphoxide.

THF refers to tetrahydrofuran.

TMEDA refers to N,N,N',N'-tetramethylethylenediamine.

TFA refers to trifluoroacetic acid.

HPLC refers to high pressure liquid chromatography.

RT refers to retention time.

Useful preparative techniques are described in WO96/09294, WO97/03069 and WO97/13771; also described in these publications are appropriate intermediate compounds other than those detailed below.

General Procedures (A) Reaction of an amine with a bicyclic species containing a 4-chloropyrimidine ring The optionally substituted bicyclic species and the specified amine were mixed in an appropriate solvent (acetonitrile unless otherwise specified), and heated to reflux. When the reaction was complete (as judged by tlc), the reaction mixture was allowed to cool. The resulting suspension was diluted, e.g. with acetone, and the solid collected by filtration, washing e.g. with excess acetone, and dried at 60° C. in vacuo, giving the product as the hydrochloride salt. If the free base was required (e.g. for further reaction), this was obtained by treatment with a base e.g. triethylamine; purification by chromatography was then performed, if required.

(B) Reaction of a product from Procedure (A) with a heteroaryl tin reagent

A stirred mixture of the product from Procedure (A), (containing a suitable leaving group such as chloro, bromo, iodo or triflate), a heteroaryl stannane and a suitable palladium catalyst, such as bis-(triphenylphosphine)palladium (II) chloride or 1,4-bis(diphenylphosphino)-butane palladium (II) chloride (prepared as described in C. E. Housecroft et. al., Inorg. Chem., (1991), 30(1), 125–130), together with other appropriate additives, were heated at reflux in dry dioxane or another suitable solvent under nitrogen until the reaction was complete. The resulting mixture was generally purified by chromatography on silica.

(C) Reaction of the product from Procedure (A) with a second amine

The product of Procedure (A) (containing a suitable leaving group such as chloro) was dissolved in an excess of the desired amine (or a solution thereof) and heated in a pressure vessel (e.g. at 130° C. for 17 hr). The cooled mixture was generally purified by chromatography on silica.

Preparation of Intermediates

1-Benzyl-5-nitro-1H-indole

Dry dimethylsulphoxide (20 ml) was added to potassium hydroxide (4.2 g, 0.074 mol) (crushed pellets) and the mixture was stirred under nitrogen for 5 mins. 5-Nitroindole (commerically available) (3.0 g, 0.019 mol) was then added and the red mixture stirred for 30 min at room temperature. The mixture was then cooled to −10° C., benzyl bromide (4.4 ml, 0.037 mol) was slowly added and the mixture stirred and allowed to warm to room temperature over a period of 40 mins. Water (50 ml) was then added and the mixture was extracted with diethyl ether (2×200 ml). The extracts were washed with water (4×50 ml), dried over sodium sulphate and evaporated to leave an oily solid. The excess benzyl bromide was removed by dissolving the whole in diethyl ether (50 ml), diluting this solution with 40–60 petrol (50 ml) and then gradually removing the diethyl ether in vacuo to leave a yellow solid suspended in the petrol. The solid was filtered, washed with copious amounts of 40–60 petrol and dried to give 1-benzyl-5-nitroindole (2.4 g, 51%) as a yellow solid, m.p. 102–104° C.; δH [$^2$H$_6$]-DMSO 8.53 (1H, s, 4-H), 8.00 (1H, d, J 9, 6-H), 7.78 (1H, s, 2-H), 7.68 (1H, d, J 9, 7-H), 7.36-7.20 (5H, m, 2'-H, 3'-H, 4'-H, 5'-H, 6'-H), 6.81 (1H, s, 3-H), 5.52 (2H, s, CH$_2$).

5-Amino-1-benzyl-1H-indole

A solution of 1-benzyl-5-nitroindole (0.51 g, 0.02 mol) in a mixture of ethyl acetate (25 ml) and methanol (25 ml) was carefully added to 10% palladium on charcoal (45 mg). The resulting suspension was stirred at room temperature under an atmosphere of hydrogen. When the reaction was complete (indicated by tlc or calculated uptake of hydrogen) the suspension was filtered through a pad of Hyflo™, and the filtrate evaporated to dryness to give 5-amino-1-benzylindole (0.40 g, 91%) as an off-white solid; m.p. 66–68° C.; δH [$^2$H$_6$]-DMSO 7.30-7.12 (6H, m, 2-H, 2"-H, 3"-H, 4"-H, 5"-H, 6"-H), 7.08 (1H, d, J 8, 7-H), 6.70 (1H, s, 4-H), 6.49 (1H, d, J 8, 6-H), 6.18 (1H, s, 3-H), 5.28 (2H, s, CH$_2$), 4.38 (2H, br s, NH$_2$).

2-Benzyl-5-nitro-1H-benzimidazole

A misture of 4-nitro-o-phenylene diamine (1.54 g) and phenylacetic acid (2.04 g) in 5N aqueous HCl (16 ml) were heated at 110° C. under nitrogen for 22 hours. The mixture was cooled to room temperature and the accumulated black solid collected by filtration. This crude residue was then adsorbed onto silica and chromatographed to give the title compound (0.84 g) as a purple foam; δH CDCl$_3$ 9.70 (1H, bs), 8.15 (1H, d), 7.30 (7H, m), 4.30 (2H, s); m/z (M+1)$^+$ 254.

5-Amino-2-benzyl-1H-benzimidazole

The title compound was prepared from 5-nitro-2-benzylbenzimidazole by an analogous reduction method to that described above for 5-amino-1benzyl-1H-indole; m/z (M+1)$^+$224. Also note the published method (J. Het. Chem., 23, 1109–13, (1986)).

1-N-Benzyl-5-nitro-1H-indzole and 2-N-Benzyl-5-nitro-1H-indazole

A stirred mixture of 5-nitroindazole (50 g), potassium carbonate (46.6 g, 1.1 equiv.) and benzyl bromide (57.6 g, 1.1 equiv) in N,N-dimethylformamide (500 ml) was heated at 75° C. for a period of 4 hours. The reaction was then cooled and water (500 ml) was gradually added to precipitate the product which was filtered off and washed with water (50 ml) and dried in the air at ambient temperature. The weight of pale yellow solid thus obtained was 72.3 g (93%), m.pt. 95–97° C.; HPLC (Partisil 5, dichloromethane, 4 ml/min, 250 nm) gave an isomer ratio (1-N-benzyl:2-N-benzyl) of 63:37 (RT-1N3.4 min, RT-2N6.6 min). To a filtered solution of the mixed regioisomers (100 g) in acetone (470 ml) at room temperature was added, gradually with stirring, water (156 ml) and the mixture was stirred for one hour. The resultant yellow crystalline solid was filtered off and dried in the air at ambient temperature to give 36.4 g (34%) of material; m.pt. 124–126° C.; HPLC showed an isomer ratio (1-N-benzyl:2-N-benzyl) of 96:4; δH (CDCl$_3$) 5.58 (2H, s, CH$_2$), 7.12-7.15(2H)&7.22-7.29(3H)-(phenyl), 7.33(1H,dt,J=1 Hz & 9 Hz, H-7), 8.15(1H,dd,J=2 Hz & 9 Hz, H-6), 8.19(1H,d,J=1 Hz, H-3), 8.67 (1H,dd,J=1 Hz & 2 Hz, H-4).

also note the published method in FR 5600, Jan. 8, 1968.

5-Amino-1-N-benzyl-1H-indazole

1-Benzyl-5-nitroindazole (400 g) was suspended in ethanol (5 liter) and hydrogenated in the presence of 5% platinum on carbon catalyst (20 g) operating at 1 bar pressure and 50–60° C. When hydrogen uptake was complete the reactor contents were heated to 70° C., discharged and filtered while still hot and the filtrate concentrated to ~4 liter which caused some crystallisation. Water (4 liter) was then gradually added with stirring and the mixture was stirred at 5° C. overnight. The resultant crystals were filtered off and air-dried at ambient temperature to give 305 g (86%) of material, m.pt. 150–152° C.; HPLC (Supelcosil ABZ+, gradient 0.05% trifluoroacetic acid in water/0.05% trifluoroacetic acid in acetonitrile, 1.5 ml/min, 220 nm) showed<1% of the corresponding 2-N-isomer (RT-1N 6.03 min, RT-2N 5.29 min); δH (CDCl$_3$) 3.3-3.8(2H,broad s,NH$_2$), 5.47 (2H,s,CH$_2$), 6.74(1H,dd,J=2 Hz & 9 Hz,H-6), 6.87(1H,dd,J=1 Hz & 2 Hz,H-4), 7.06-7.11(3H) & 7.17-7.25(3H)-(phenyl & H-7), 7.77(1H,d,J=1 Hz, H-3).

Also note the published method in FR 5600, Jan. 8, 1968.

1-Benzyl-3-methyl-5-nitro-1H-indazole

2-Fluoro-5nitroacetophenone (H. Sato et al, Bioorganic and Medicinal Chemistry Letters, 5(3), 233–236, 1995) (0.24 g) was treated with triethylamine (0.73 ml) and benzyl hydrazine dihydrochloride (0.255 g) in ethanol (20 ml) at reflux under N$_2$ for 8 days. The mixture was cooled and the solid 1-benzyl-3-methyl-5-nitroindazole (0.16 g) was collected by filtration; m/z (M+1)$^+$268.

1-Benzyl-3-methyl-1H-indazol-5-ylamine

1-Benzyl-3-methyl-5-nitroindazole (0.15 g) in THF (15 ml) was treated with platinum on carbon (0.05 g, 5%) under an atmosphere of hydrogen at room temperature. When hydrogen uptake was complete, the mixture was filtered and concentrated in vacuo to give the title compound; m/z (M+1)$^+$268.

Further amino-indazole intermediates

The relevant nitro-substituted 1H-indazole was treated with a base such as potassium carbonate or sodium hydroxide in a suitable solvent, such as acetone or acetonitrile. The appropriate aryl halide or heteroaryl halide was added and the reaction mixture heated or stirred at room temperature overnight. Subsequent concentration in vacuo and chromatography on silica gave the desired 1-substituted nitro-1H-indazoles. Hydrogenation was carried out by analogy with the preparation of 5-amino-1benzyl-1H-indole described above.

Amines prepared by such methods and specifically used in the preparation of the later Examples include:

5-Amino-1-benzyl-1H-indazole; m/z (M+1)$^+$224

5-Amino-1-(2-fluorobenzyl)-1H-indazole; m/z (M+1)$^+$ 242

5-Amino-1-(3-fluorobenzyl)-1H-indazole; m/z (M+1)$^+$ 242

5-Amino-1-(4-fluorobenzyl)-1H-indazole; m/z (M+1)$^+$ 242

5-Amino-1-(2-pyridylmethyl)-1H-indazole; m/z (M+1)$^+$ 225

5-Amino-1-(3-pyridylmethyl)-1H-indazole; m/z (M+1)$^+$ 225

5-Amino-1-(2,3-difluorobenzyl)-1H-indazole; m/z (M+1)$^+$260

5-Amino-1-(3,5-difluorobenzyl)-1H-indazole; m/z (M+1)$^+$260.

Other amines prepared by such methods include:

5-Amino-1-(4-pyridylmethyl)-1H-indazole; m/z (M+1)$^+$ 225

1-Benzenesulphonylindol-5-yl-amine was prepared according to the published method (J. Org. Chem., 55, 1379–90, (1990)).

3-Benzenesulphonylindol-6-yl-amine

3-Benzenesulphonyl-6-nitroindole (K. Wojciechowski and M Makosza, Tet. Lett., 25 (42), p4793, 1984) was hydrogenated by analogy with the procedures above to give the title compound; $\delta$H [$^2$H$_6$]DMSO 11.64 (1H,s), 7.94 (2H,m), 7.81 (1H,s), 7.57 (3H, m), 7.49(1H,d), 6.60(1H,s), 6.55 (1H,dd), 5.40 (2H,s).

N-5-[N-tert-Butoxycarbonyl)amino]-2-chloropyridine

A stirred solution of 6-chloronicotinic acid (47.3 g), diphenylphosphoryl azide (89.6 g) and triethylamine (46 ml) in t-butanol (240 ml) were heated under reflux under nitrogen for 2.5 hours. The solution was cooled and concentrated in vacuo. The syrupy residue was pured into 3 liters of a rapidly stirred solution of 0.33N aqueous sodium carbonate. The precipitate was stirred for one hour and filtered. The solid was washed with water and dried in vacuo at 70° C. to give the title compound (62 g) as a pale brown solid; m.p. 144–146° C.; $\delta$H [$^2$H$_6$]-DMSO 8.25(1H,d), 7.95 (1H,bd), 7.25 (1H,d), 6.65(1H,bs), 1.51 (9H,s); m/z (M+1)$^+$229.

This material may subsequently be carried forward to the appropriately substituted pyridopyrimidine intermediate according to the procedures as described in WO95/19774, J. Med. Chem., 1996, 39, pp 1823–1835, and J. Chem. Soc., Perkin Trans. 1, 1996, pp 2221–2226. Specific compounds made by such procedures include 6-chloro-pyrido[3,4-d] pyrimidin-one and 4,6-dichloro-pyrido[3,4-d]pyrimidine.

2-N,N-Dimethylamino-4-nitropyridine

2-Chloro-4-nitropyridine (0.64 g) was treated with aqueous dimethylamine (10 ml, 25%) at reflux for 30 minutes. The mixture was diluted with water and filtered. The solid was washed with water and dried in vacuo to give the title compound (0.67 g); $\delta$H [$^2$H$_6$]DMSO 9.05 (1H,d), 8.30(1H, dd), 6.84(1H,d), 3.28 (6H,s).

2-N,N-Dimethylamino-4-aminopyridine

2-N,N-Dimethylamino-4-nitropyridine (0.67 g) in ethanol (50 ml) was added to 10% palladium on charcoal and stirred under an atmosphere of hydrogen. When the reaction was complete, the suspension was filtered through a pad of Hyflo™ and the filtrate concentrated in vacuo to give the title compound (0.49 g); $\delta$H [$^2$H$_6$]DMSO 7.57 (1H,d), 6.88(1H,dd), 6.41(1H,d), 4.39(2H,bs), 3.80 (6H,s); m/z (M+1$^+$)138.

N-(4-N',N'-Dimethylaminopyrid-3-yl)-2,2-dimethylpropionamide

2-N,N-Dimethylamino-4aminopyridine (1.37 g) in methylene chloride (20 ml) under N$_2$ was treated with triethylamine (1.53 ml) and pivaloyl chloride (1.32 g) over 5 minutes. After 16 hours at room temperature, the mixture was diluted with methylene chloride, washed with water, dried and concentrated to give the title compound (2.2 g); $\delta$H [$^2$H$_6$]DMSO 9.20(1H,s), 8.22 (1H,d), 7.70(1H,dd), 6.60 (1H,d), 2.98(6H,s), 1.20 (9H,s); m/z (M+1$^+$)222.

2(N,N-Dimethylamino)-5-(2,2-dimethylpropionamido)-pyridine-4-carboxylic acid

N-(4-N',N'-Dimethylaminopyrid-3-yl)-2,2-dimethylpropionamide (1.1 g) in dry THF under N$_2$ at −70° C. was treated with TMEDA (1.45 g) and butyl lithium (1.6M, 8 ml). The mixture was warmed to 0° C. for three hours before being recooled to −70° C. Carbon dioxide was bubbled through the solution for 1 hour and the resulting solution was warmed to room temperature under a carbon dioxide atmosphere and stirred there for 16 hours. The resulting mixture was concentrated in vacuo and partitioned between ether and water. The aqueous layer was concentrated in vacuo to give the title compound (1.0 g); $\delta$H [$^2$H$_6$]DMSO 13.50(1H,s), 9.22(1H,s), 7.26(1H,s), 2.95(6H, s), 1.20 (9H,s); m/z (M+1$^+$)266.

5-Amino-2-(N,N-dimethylamino)-pyridine-4-carboxylic acid 2-(N,N-Dimethylamino)-5-(2,2-dimethylpropionamido)-pyridine-4-carboxylic acid (0.8 g) was treated with 5N HCl at reflux for 5 hours. The mixture was allowed to cool and evaporated to dryness to give the title compound (0.54 g);$\delta$H [$^2$H$_6$]DMSO 8.15(1H,s), 7.35(2H,bs), 6.70(1H,s), 3.10(6H, s); m/z (M+1$^+$)182.

6-(N,N-Dimethylamino)-pyrido[3,4-d]pyrimidin-4-one

5-Amino-2-(N,N-dimethylamino)-pyridine-4-carboxylic acid (0.54 g) was treated with formamidine acetate (3.12 g) in glacial acetic acid (20 ml) and heated at reflux for 16 hours. The mixture was cooled, evaporated to dryness in vacuo and partitioned between ethyl acetate and water. The organic phase was separated, dried over magnesium sulphate and concentrated in vacuo to give, after chromatography on silica, the title compound (0.25 g); $\delta$H CDCl$_3$ 9.10(1H,d), 8.80(1H,s), 8.31(1H,s), 7.07(1H,s), 3.20(6H,s); m/z (M+1$^+$)191.

Alternatively, 6-chloro-pyrido[3,4-d]pyrimidin-4-one (26.14 g) was treated with 2N dimethylamine in ethanol (200 ml) and heated at 130° C. in a Parr bomb for 3 days. The cooled mixture was filtered and triturated from isopropanol to give the title compound (16.61 g) as a yellow solid; m/z (M+1$^+$)191.

4-Chloro-6-(N,N-dimethylamino)-pyrido[3,4-d] pyrimidine

6(N,N-Dimethylamino)-pyrido[3,4-d]pyrimidin-4-one (12 g) was carefully treated with phosphorus oxychloride (42 ml) and triethylamine (18 ml) at room temperature under N$_2$. After 1 hour at room temperature and 1 hour at 50° C., the mixture was concentrated in vacuo, azeotroping with toluene, then taken up in ethyl acetate, washed with sodium bicarbonate solution, dried and concentrated in vacuo to give the title compound (10.34 g); δH CDCl₃ 9.13(1H,s), 8.74(1H,s), 6.69(1H,s), 3.25(6H,s).

6-Cyano-pyrido[3,4-d]pyrimidin-4-one

6-Chloro-pyrido[3,4-d]pyrimidin-4-one (10 g) in 1-methyl-2-pyrrolidinone (100 ml) was treated with copper (I) iodide (10.52 g) and potassium cyanide (7.10 g) at 215° C. for 72 hours under N₂. Further potassium cyanide was added (3.58 g) and heating continued at 230° C. for 70 hours. The 1-methyl-2-pyrrolidinone was removed by distillation at reduced pressure and the residue absorbed onto silica. Chromatography gave the title compound (2.4 g) as a beige solid; δH [²H₆]DMSO 13.0(1H, bs), 9.25 (1H,s), 8.55 (1H,s), 8.50 (1H,s); m/z (M+1⁺)171.

6-(1,2,3,4-Tetrazol-5-yl)-pyrido[3,4-d]pyrimidin-4-one

6-Cyano-pyrido[3,4-d]pyrimidin-4-one (0.3 g) in diglyme (2 ml) was treated with tributyl tin azide (0.49 g) at reflux under N₂ for 15 hours. The cooled mixture was partitioned between ethyl acetate and water and the aqueous phase extracted further with ethyl acetate. The aqueous phase was concentrated in vacuo, the residue taken up in methanol and inorganics removed by filtration. Subsequent concentration gave the title compound (1.4 g) as a beige solid; δH [²H₆]DMSO 8.96 (1H,s), 8.50 (1H,s), 8.27 (1H,s); m/z (M+1⁺)216.

6-(5-Methyl-1,3,4-oxadiazol-2-yl)-pyrido[3,4-d]pyrimidin-4-one 6-(1,2,3,4-Tetrazol-5-yl)-pyrido[3,4-d]pyrimidin-4-one (1.4 g) in acetic anhydride (10 ml) was heated at reflux under N₂ for 2.5 hours. The cooled mixture was absorbed onto silica and purified by chromatography to give the title compound 90.14 g) as a beige solid; δH [²H₆]DMSO 13.0(1H,bs), 9.30 (1H,s), 8.66 (1H,s), 8.47 (1H,s) 2.75 (3H,s); m/z (M+1⁺)230.

4-Chloro-6-(5-methyl-1,3,4-oxadiazol-2-yl)-pyrido[3,4-d]pyrimidine 6-(5-Methyl-1,3,4-oxadiazol-2-yl)-pyrido[3,4-d]pyrimidin-4-one (0.5 g) was treated with phosphorus oxychloride at room temperature under N₂. After 1 hour at room temperature and 1 hour at 50° C., the mixture was concentrated in vacuo, azeotroping with toluene, then taken up in ethyl acetate, washed with sodium bicarbonate solution, dried and concentrated in vacuo to give the title compound (0.17 g) as an orange solid; δH CDCl₃ 9.68 (1H,s), 9.30 (1H,s), 8.96 (1H,s), 2.75 (3H,s); m/z (M+1⁺)248.

6-Benzyloxy-4-hydroxy-pyrido[3,4-d]pyrimidine

Sodium hydride (8.14 g of 60% dispersion with mineral oil, 203.5 mmol) was suspended in bensyl alcohol (200 ml) under a nitrogen atmosphere. 6-Chloropyrido[3,4-d]pyrimidine (9.081 g, 50.0 mmol) was added and the mixture was heated at 150° C. for 18 hours. When cool, the mixture was partitioned between water (200 ml) and ether (200 ml), the layers were separated, and the aqueous layer was washed with further ether. The aqueous solution was then acidified to pH1 by the addition of dilute HCl causing the precipitation of the title compound as a cream solid (7.885 g, 31.1 mmol, 62%); δH [²H₆]DMSO 8.71(1H,s), 7.89(1H,s), 7.25-7.48 (6H,m), 5.40 (2H,s); m/z (M+1⁺)254.

6-Benzyloxy-4-chloro-pyrido[3,4-d]pyrimidine

6-Benzyloxy-4-hydroxy-pyrido[3,4-d]pyrimidine (1.033 g, 4.1 mmol) was suspended in thionyl chloride (10 ml) under a nitrogen atmosphere. DMF (3 drops) was added and the mixture was heated to reflux with stirring for 5.5 hours to give a dark solution, and then left to stand under nitrogen overnight. The mixture was concentrated in vacuo, azeotroping twice with toluene to remove all traces of thionyl cloride and acidic by-products. The material was further dried for two hours in vacuo to give the title compound as a brown solid, used without further purification; δH [²H₆]DMSO 8.77(1H,s), 8.13(1H,s), 7.30-7.52 (6H,m), 5.45 (2H, s).

(3-Methyl-3-oxetane)methyl 2-furoate

2-Furoic acid (9.0 g, 80.3 mmol) was added to a solution of 3-methyl-3-oxetanemethanol (16.5 g, 161.6 mmol), 1,3-dicyclohexylcarbodiimide (25.0 g, 121.1 mmol) and DMAP (0.50 g, 4.1 mmol) in dichloromethane (250 ml), and the mixture was stirred under a nitrogen atmosphere overnight. The mixture was filtered, and the filtrate was concentrated in vacuo to give an oil. Crystallisation from ethanol/water gave a white solid collected by filtration, which was shown by NMR to be 2-furoic acid. The filtrate was concentrated in vacuo to remove the ethanol, and the resulting aqueous solution was extracted with dichloromethane (x2). The combined dichloromethane extracts were dried (MgSO₄) and concentrated to give the title compound as a colourless oil (11.8 g, 60.1 mmol, 75%); δH [²H₆]DMSO 8.00 (1H,s), 7.34 (1H,d), 7.71 (1H,dd), 4.44 (2H,d), 4.35 (2H,s), 4.28 (2H,d), 1.31 (3H,s).

2-(4-Methyl-2,6,7-trioxabicyclo[2,2,2]oct-1-yl)furan

3-Methyl-3-oxetane)methyl 2-furoate (11.8 g, 60.1 mmol) was dissolved in dichloromethane (250 ml) and the solution was cooled to 0° C. Boron trifluoride-etherate (10 drops) was added and the mixture stirred at room temperature, and then left to stand for two months. Triethylamine (0.5 ml, 0.36 g, 3.6 mmol) was added and the mixture concentrated to give a sticky white solid. Trituration with ether/acetone gave the title compound as a white solid (2.2 g, 11.2 mmol, 19%); δH [²H₆]DMSO 8.00 (1H,s), 7.34 (1H,d), 7.71 (1H, dd), 4.44 (2H,d), 4.35 (2H,s), 4.28 (2H,d), 1.31 (3H,s).

5-(4-Methyl-2,6,7-trioxabicyclo[2,2,2]oct-1-yl)-2-[tri(n-butyl)stannyl]furan 2-(4-Methyl-2,6,7-trioxabicyclo[2,2,2]oct-1-yl)furan (2.0 g, 10.2 mmol) was dissolved in THF (20 ml) and the solution was cooled to −78° C. n-Buli (1.6M solution in hexanes, 7.7 ml, 12.32 mmol) was added and the mixture stirred at −78° C. for 30 min, allowed to warm to 0° C. for 20 min. and then recooled to −78° C. The tributyltin chloride (3.5 ml, 4.68 g, 14.4 mmol) was added and stirring was continued at −78° C. for 15 min. The mixture was allowed to warm gradually to room temperature and stirring continued for three days. The reaction was quenched by the addition of water, and extracted with ethyl acetate. This solution was washed with water, dried (MgSO₄), and concentrated in vacuo to give the title compound as a yellow oil (4.7 g, 9.7 mmol, 95%); δH [²H₆]DMSO 6.52 (1H,d), 6.38 (1H,d), 3.96 (6H,s), 0.77-1.63 (30H,m).

(1-Benzyl-1H-indazol-5-yl)-(6-[5-(4-methyl-2,6,7-trioxabicyclo[2,2,2]oct-1-yl)-furan-2-yl]-pyrido-[3,4-d]pyrimidin-4-yl)-amine 1-Bensyl-1H-indazol-5-yl)-(6-chloro-pyrido-[3,4-d]pyrimidin-4-yl)-amine (0.425 g, 1.10 mmol), 5-(4-methyl-2,6,7-trioxa-bicyclo[2,2,2]oct-1-yl)-2-[tri(n-butyl)stannyl]furan (1.95 g, 4.0 mmol) and 1,4-bis(diphenylphosphino)butane palladium (II) chloride (0.068 g, 0.11 mmol) were reacted in dry dioxane (15 ml) according to Procedure B. Purification by silica gel chromatography, eluting with 50–100% ethyl acetate/i-hexane, gave the title compound as a yellow solid (0.451 g, 0.929 mmol, 86%); δH [²H₆]DMSO 10.58 (1H,s), 9.14 (1H,s), 8.71 (1H,s), 8.61 (1H,s), 8.16-8.21 (2H,m), 7.68-7.79 (2H,m), 7.22-7.36 (5H,m), 7.13 (1H,d), 6.68 (1H,d), 5.69 (2H,s), 4.06 (6H,s), 0.86 (3H,s); m/z (M+1⁺)547.

EXAMPLES

Example 1

(1-Benzyl-1H-indazol-5-yl)-(6-chloro-pyrido[3,4-d]pyrimidin-4-yl)-amine hydrochloride Prepared according to Procedure A from 1-benzyl-1H-indazol-5-ylamine and 4,6-dichloro-pyrido[3,4-d]pyrimidine; δH [²H₆]DMSO 9.08 (1H,s), 8.92 (1H,s), 8.82

(1H,s), 8.23 (1H,d), 8.19 (1H,s), 7.80 (1H,d), 7.70 (1H,dd), 7.38-7.22 (5H,m), 5.69 (2H,s); m/z (M+1)⁺387.

Example 2

N4-(1-Bensyl-1H-indazol-5-yl)-N6,N6-dimethyl-pyrido[3,4-d]pyrimidine-4,6-diamine A stirred solution of (1-benzyl-1H-indazol-5-yl)-(6-chloro-pyrido[3,4-d]pyrimidin-4-yl)-amine (0.5 g) in 33% aqueous dimethylamine (5 ml) was heated at 130° C. in a reacti-vial for 17 hr. The cooled mixture was dissolved in chloroform, absorbed onto silica and chromatographed to give the title compound (Procedure C) as a yellow solid; δH [$^2$H$_6$]DMSO 9.00(1H,s), 8.51(1H,s), 8.09(2H,d), 7.55(1H, dd), 7.25(7H,m), 6.39(1H,m), 5.60(2H,s) 3.20 (6H,s); m/z (M+1)⁺396.

Alternatively, 4-chloro-6-(N,N-dimethylamino)-pyrido[3,4-d]pyrimidine and 5-amino-1-benzyl-1H-indazole were reacted according to Procedure A to give the title compound as the hydrochloride salt; δH [$^2$H$_6$]DMSO 11.82(1H,s), 8.95(1H,s), 8.63(1H,s), 8.25(1H,s), 8.15(1H,s), 7.87(1H,d), 7.78(1H,s), 7.70(1H,dd), 7.30(5H,m), 5.79(2H,s), 3.23(6H, s); $C_{23}H_{22}N_7$cl requires C 63.96%, H 5.13%, N 22.70%; found C 63.44%, H 4.99%, N 22.74%.

The hydrochloride salt was partitioned between dichloromethane and 2N sodium carbonate. Extraction of the aqueous layer with dichloromethane was followed by drying of the organic phase and concentration in vacuo to give the free base.

Example 3

(1-Benzyl-1H-indazol-5-yl)-6-(N-(2-hydroxyethyl)-N-methylamino)-pyrido[3,4-d]pyrimidin-4-yl)-amine A stirred solution of (1-Benzyl-1H-indazol-5-yl)-(6-chloro-pyrido[3,4-d]pyrimidin-4-yl)-amine (0.2 g) in 2-methylaminoethanol (4 ml) was heated at 130° C. in a reacti-vial for 96 hr (Procedure C). The cooled mixture was partitioned between ethyl acetate and water. The aqueous phases were extracted with ethyl acetate. The dried extracts were concentrated in vacuo and the residue purified by flash chromatography to give the title compound as a yellow solid;δH [$^2$H$_6$]DMSO/CDCl$_3$ 9.00(1H,s), 8.85(1H,s), 8.45 (1H,s), 8.10(2H,d), 7.64(1H,dd), 7.30(7H,m), 7.08(1H,s), 5.60(2H,s), 3.85(4H,m) 3.25(3H,s); m/z (M+1)⁺426.

Example 4

(1-Bensyl-1H-indazol-5-yl)-(pyrido[3,4-d]pyrimidin-4-yl)-amine

A stirred solution of (1-Benzyl-1H-indazol-5-yl)-(6-chloro-pyrido[3,4-d]pyrimidin-4-yl)-amine (0.165 g), 2-(tri-n-butylstannyl)furan (0.139 g) and bis-(triphenylphosphine)palladium (II) chloride (30 mg) in dioxane (10 ml) was heated at reflux under nitrogen for 65 hr (Procedure B). The cooled mixture was absorbed onto silica and chromatographed to give the title compound as an orange solid; δH CDCl$_3$ 9.34(1H,s), 8.82(1H,s), 8.70(1H,d), 8.15(1H,d), 8.10 (1H,s), 7.65(1H,d), 7.60(1H,s), 7.53(1H,dd), 7.40(1H,d), 7.25(6H,m), 5.60(2H,s); m/z (M+1)⁺353.

Example 5

(2-Bensyl-1H-benzimidazol-5yl)-(6-chloro-pyrido[3,4-d]pyrimidin-4-yl)-amine

Prepared according to Procedure A from 5-amino-2-bensyl-1H-benzimidazole and 4,6-dichloro-pyrido[3,4-d]pyrimidine; δH [$^2$H$_6$]-DMSO 9.13(1H,s), 8.93(1H,s), 8.84 (1H,s), 8.60(1H,s), 8.05(1H,dd), 7.88(2H,d), 7.50(6H, m), 4.61(2H,s); m/z (M+1)⁺387.

Example 6

N4-(1-Benzyl-1H-indol-5-yl)-N6, N6-dimethyl-pyridol[3,4-pyrimidine-4,6-diamine

The title compound was prepared from (1-benzyl-1H-indol-5-yl)-(6-chloro-pyrido(3,4-d]pyrimidin-4-yl)-amine by an analogous method to Example 2 (Procedure C) as a yellow solid; δH CDCl$_3$8.98(1H,s), 8.50(1H,s), 7.93(1H,s), 7.30(5H,m), 7.15(2H,m), 6.60(1H,d), 6.38(1H,s), 5.35(2H, s), 3.20(6H,s); m/z (M+1)⁺395.

Example 7

N4-(2-Benzyl-1H-benzimidazol-5-yl)-N6, N6-dimethyl-pyrido[3,4-d]-pyrimidine-4,6-diamine The title compound was prepared from (2-benzyl-1H-benzimidazol-5-yl)-(6-chloro-pyrido[3,4-d]pyrimidin-4-yl)-amine by an analogous method to Example 2 (Procedure C) as a yellow solid: δH [$^2$H$_6$]-DMSO 9.75(1H,s), 8.80(1H,s), 8.32(1H,s), 8.08(1H,bs), 7.50(2H,m), 7.30(5H,m), 4.20(2H, s); m/z (M+1)⁺396.

Example 8

(1-Benzyl-1-H-indazol-5-yl)-(6-(5-[1,3-dioxolan-2-yl]-furan-2-yl)-pyrido[3,4-d]-pyrimidin-4-yl)-amine (1-Benzyl-1H-indazol-5-yl)-(6-chloro-pyrido[3,4-d]pyrimidin-4-yl)-amine (4.28 g), 2-(tributylstannyl)-5-(1,3-dioxolan-2-ylmethyl)-furan (J. Chem Soc., Chem. commun., (1988), p560) (10 g) and 1,4-bis(diphenylphosphino)butane palladium (II) chloride (1 g) were heated at reflux in dioxane (150 ml) for 24 hr (Procedure B). The solvent was removed in vacuo and the residue chromatographed on silica. Subsequent trituration gave the title compound as a yellow solid: δH [$^2$H$_6$]-DMSO 10.46 (1H,s), 9.17 (1H,s), 8.74 (1H,s), 8.52 (1H,s), 8.23 (1H,s), 8.18 (1H,s), 7.80-7.68 (2H,m), 7.41-7.22 (5H,m), 7.17 (1H,d), 6.80 (1H,d), 6.06 (1H,s), 5.71 (2H,s), 4.20-3.96 (4H,m).

Example 9

5-(4-(1-Benzyl-1H-indazol-5-ylamino)-pyrido[3,4-d]pyrimidin-6-yl)-furan-2-carbaldehyde (1-Benzyl-1H-indazol-5-yl)-(6-(5-[1,3-dioxolanyl]-furan-2-yl)-pyrido[3,4-d]-pyrimidin-4-yl)-amine (3.03 g) and 2N HCl (50 ml) were stirred in THF (50 ml) for 16 hr. The resulting precipitate was filtered and washed with water to give the thehydrochloride salt of the product; δH [$^2$H$_6$] DMSO 11.70 (1H,s), 9.74 (1H,s) 9.30 (1H,s), 9.27 (1H,s), 8.85 (1H,s), 8.23 (1H,s), 8.18 (1H,s), 7.68-7.87 (3H,m), 7.55 (1H,d), 7.22-7.38 (5H,m), 5.71 (2H,s). Subsequent neutralisation with triethylamine in ethanol/water gave the title compound; δH[$^2$H$_6$]-DMSO 9.64(1H,s), 9.19 (1H,s), 9.09 (1H,s), 8.72(1H,s), 8.12(2H,m), 7.71(2H,m), 7.63(1H,dd), 7.43(1H,d), 7.20(5H,m), 5.62(2H,s).

Example 10

(2S)-1-(5-(4-(1-Benzyl-1H-indazol-5-ylamino)-6-pyrido[3,4-d]pyrimidin-6-yl)-furan-2-ylmethyl)-pyrrolidine-2-carboxylic acid amide hydrochloride 5(4-(1-Benzyl-1H-indazol-5-ylamino)-pyrido[3,4-d]pyrimidin-6-yl)-furan-2-carbaldehyde (800 mg) and L-prolinamide (1.0 g) were mixed in dichloromethane (8 ml)

at 25° C. for 1 hr. The solution was cooled to 0° C. and sodium triacetoxyborohydride (2.0 g) was added. After 4 hr at 25° C. the reaction mixture was subjected to flash chromatography directly on silica using 3% methanol in chloroform, to give the free base as yellow solid; δH [$^2$H$_6$]DMSO 10.33 (1H,s), 9.13 (1H,s) 8.65 (1H,s), 8.61 (1H,s), 8.26 (1H,s), 8.16 (1H,s), 7.75 (2H,m), 7.12-7.33 (7H,m), 7.09 (1H,d), 6.56 (1H,d), 5.69 (2H,s), 3.84 (2H,s), 3.31–3.39 (1H, obscured by water), 3.09–3.14 (2H,m), 1.70–2.20 (4H,m); m/z (M+1$^+$) 545. Treatment with saturated HCl in ethyl acetate gave the title compound; δH [$^2$H$_6$]-DMSO 12.25 (1H,s), 9.52(1H,s), 9.27 (1H,s), 8.80 (1H,s), 8.53(1H,s), 8.27(1H,s), 8.21(1H,s), 7.83(2H,m), 7.72(1H, s), 7.30(6H, m), 6.93(1H, d), 6.72(2H, s), 4.88(1H, m), 4.60(2H,s), 3.20(2H, s), 1.90(4H, m); m/z (M+1)$^+$545.

Example 11

(1-Benzyl-1H-indazol-5-yl)-(6-(3-methyl-3H-imidazol-4-yl)-pyrido[3,4-d]pyrimidin-4-yl)-amine (1-Benzyl-1H-indazol-5-yl)-(6-chloro-pyrido[3,4-d]pyrimidin-4-yl)-amine (0.70 g, 1.81 mmol), 1-methyl-5-[tri(n-butyl)stannyl]imidazole (prepared according to the published method: K. Gaare et. al., Acta Chem. Scand., (1993), 47(1), p57–62) (2.2 g, 6 mmol), 1,4-bis (diphenylphosphino)-butane palladium (II) chloride (0.41 g, 0.7 mmol) and silver oxide (0.22 g, 1.8 mmol) were reacted in dry dioxane according to Procedure B. Purification by silica gel chromatography, eluting with 10%MeOH/EtOAc, gave the product as a pale brown solid (0.16 g, 0.37 mmol, 20%); δH CDCl$_3$10.62 (1H,s), 9.25 (1H,s), 8.75 (1H,s), 8.60 (1H,s), 8.13 (1H,s), 8.03 (1H,s), 7.20–7.78 (9H,m), 5.61 (2H,s), 3.96 (3H,s); m/z (M+1$^+$) 433.

Example 12

N6, N6-Dimethyl-N4-(1-pyridin-2-ylmethyl-1H-indazol-5-yl)-pyrido[3,4-d]pyrimidine-4,6-diamine hydrochloride Prepared according to Procedure A from 1-(2-Pyridylmethyl)indazol-5-ylamine and 4-chloro-6-(N,N-dimethylamino)-pyrido[3,4-d]pyrimidine; δH[$^2$H$_6$]DMSO 11.75(1H,s), 9.92(1H,s), 8.62(1H,s), 8.55(1H,d), 8.24(1H, s), 8.14(1H,s), 7.75(4H,m), 7.33(1H,m), 7.08(1H,d), 5.82 (2H,s), 3.20(6H,s); m/z (M+1$^+$) 397.

Example 13

N6,N6-Dimethyl-N4-(1-pyridin-3-ylmethyl-1H-indazol-5-yl)-pyrido[3,4]-pyrimidine-4,6-diamine hydrochloride Prepared according to Procedure A from 1-(3-Pyridylmethyl)-1H-indazol-5-ylamine and 4-chlor-6-(N,N-dimethylamino)-pyrido[3,4-d]pyrimidine; δH [$^2$H$_6$]DMSO 11.50 (1H,s), 9.90(1H,s), 8.65(1H,d), 8.60(2H,m), 8.25(1H, s), 8.14(1H,s), 7.91(1H,d), 7.75 (2H,m), 7.70(1H,s), 7.50 (1H,m), 5.80(2H,s), 3.20(6H,s); m/z (M+1$^+$) 397.

Example 14

N4-(1-Benzyl-3-methyl-1H-indazol-5-yl)-N6,N6-dimethyl-pyrido[3,4-d]pyrimidine-4,6-diamine Prepared according to Procedure A from 1-Benzyl-3-methyl-1H-indazol-5-ylamine and 4-chloro-6-(N,N-dimethylamino)-pyrido[3,4-d]pyrimidine; δH [$^2$H$_6$]DMSO 11.75 (1H,s), 8.90(1H,s), 8.62(1H,s), 8.02(1H,s), 7.70(3H, m), 7.30(5H,m), 5.62(2H,s), 3.30(6H,s) 2.50(3H,s); m/z (M+1$^+$) 410.

Example 15

N4-(1-(2-Fluoro-benzyl)-1H-indazol-5-yl)-N6,N6-dimethyl-pyrido[3,4-d]pyrimidine-4,6-diamine hydrochloride Prepared according to Procedure A from 1-(2-Fluorobenzyl)-1H-indazol-5-ylamine and 4-chloro-6-(N,N-dimethylamino)-pyrido[3,4-d]pyrimidine; δH [$^2$H$_6$]DMSO 11.45 (1H,s), 8.90(1H,s), 8.63(1H,s), 8.24(1H,s), 8.13(1H, s), 7.87(1H,d), 7.70(1H,d), 7.62(1H,s) 7.36(1H,m), 7.20 (3H,m), 5.75 (2H,s), 3.22(6H,s); m/z (M$^+$) 413.

Example 16

N4-(1-(3-Fluoro-benzyl)-1H-indazol-5-yl)-N6,N6-dimethyl-pyrido[3,4-d]pyrimidine-4,6-diamine hydrochloride N4-(1-(3-Fluoro-benzyl)-1H-indazol-5-yl)-N6,N6-dimethyl-pyrido[3,4-d]pyrimidine-4,6-diamine hydrochloride Prepared according to Procedure A from 1-(3-Fluorobenzyl)-1H-indazol-5-ylamine and 4-chloro-6-(N,N-dimethylamino)-pyrido[3,4-d]pyrimidine; δH [$^2$H$_6$]DMSO 11.52 (1H,s), 8.90(1H,s), 8.60(1H,s), 8.24(1H,s), 8.14(1H, s), 7.85(2H,m), 7.70(1H,d), 7.49(1H,s) 7.10(3H,m), 5.72 (2H,s), 3.19(6H,s); m/z (M+1$^+$) 414.

Example 17

N4-(1-(4-Fluoro-benzyl)-1H-indazol-5-yl)-N6,N6-dimethyl-pyrido[3,4-d]pyrimidine-4,6-diamine hydrochloride Prepared according to Procedure A from 1-(3-Fluorobenzyl)-1H-indazol-5-ylamine and 4-chloro-6-(N,N-dimethylamino)-pyrido[3,4-d]pyrimidine; δH [$^2$H$_6$]DMSO 11.42 (1H,s), 8.90(1H,s), 8.60(1H,s), 8.22(1H,s), 8.14(1H, s), 7.86(1H,d), 7.65(1H,d), 7.61(1H,s) 7.32(2H,dd), 7.17 (2H,dd), 5.70(2H,s), 3.23(6H,s); m/z (M$^+$) 414.

Example 18

N4-(1-Benzenesulphonyl-1H-indol-5-yl)-N6,N6-dimethyl-pyrido[3,4-d]pyrimidine-4,6-diamine hydrochloride Prepared according to Procedure A from 1benzenesulphonyl-1H-indol-5-ylamine and 4-chloro-6-(N, N-dimethylamino)-pyrido[3,4-d]pyrimidine; δH [$^2$H$_6$] DMSO 11.64 (1H,s), 8.90(1H,s), 8.60(4H,m), 7.90(1H,d), 7.65(5H,m), 6.92(1H,d) 3.20(6H,s); m/z (M$^+$) 445.

Example 19

N4-(3-Benzenesulphonyl-1-H-indol-5-yl)-N6,N6-dimethyl-pyriko[3,4-d]pyrimidine-4,6-diamine hydrochloride Prepared according to Procedure A from 3-benzenesulphonyl-1-H-indol-6-ylamine and 4-chloro-6-(N,N-dimethylamino)-pyrido[3,4-d]pyrimidine; δH [$^2$H$_6$] DMSO 11.55 (1H,s), 11.50(1H,s), 8.90(1H,s), 8.60(1H,d), 8.79(1H,d), 8.00(3H,m), 7.86(1H,d) 7.60(5H,s), 3.20(6H,s); m/z (M$^+$) 445.

Example 20

(1-Benzyl-1H-indazol-5-yl)-(6-imidazol-1-yl-pyrido [3,4]pyrimidin-4-yl)-amine

Imidazole (0.8 g) in dry DMSO was treated with sodium hydride (60%, 0.47 g) and (1-Benzyl-1H-indazol-5-yl)-(6- chloro-pyrido[3,4-d]pyrimidin-4-yl)-amine in a reacti-vial and heated at 120° C. After 7 days, the mixture was poured onto water and extracted with ethyl acetate. Purification using a Bond Elute™ cartridge gave the title compound as a brown solid after trituration from water; δH [$^2$H$_6$]DMSO 10.28 (1H,s), 9.25(1H,s), 8.90(1H,s), 8.78(1H,s), 8.67(1H,s), 8.30(1H,s), 8.10(1H,s) 7.88(2H,m), 7.40(5H,s), 5.70(2H,s); m/z (M$^+$) 419.

Example 21

(1-Benzyl-1H-indazol-5-yl)-(6-(1,2,4-triazol-1-yl-pyrido[3,4]pyrimidin-4-yl)-amine 1,2,4-triazole was reacted with (1-Benzyl-1H-indazol-5-yl)-(6-chloro-pyrido[3,4-d]pyrimidin-4yl)-amine as in Example 20 to give the title compound; δH [$^2$H$_6$]DMSO 10.53 (1H,s), 9.46(1H,s), 9.14(1H,s), 9.01(1H,s), 8.40(1H,s), 8.25(1H,s), 8.15(1H,s) 7.75(2H,s), 7.25(5H,m), 5.65(2H,s); m/z (M$^+$) 418.

Example 22

(1-Benzyl-1H-indazol-5-yl)-(6-(1,2,3-triazol-2-yl-pyrido[3,4]pyrimidin-4-yl)-amine 1,2,3-triazole was reacted with (1-Benzyl-1H-indazol-5-yl)-(6-chloro-pyrido[3,4-d]pyrimidin-4yl)-amine as in Example 21 to give the title compound; δH [$^2$H$_6$]DMSO 10.62 (1H,s), 9.24(1H,s), 8.73(1H,s), 8.33(1H,s), 8.21(1H,s), 7.80(1H,s), 7.33(5H,m), 5.73(2H,s); m/z (M$^+$) 420.

Example 23

(1-Benzyl-1H-indazol-5-yl)-(6-(1,2,3-triazol-1-yl-pyrido[3,4]pyrimidin-4-yl)-amine 1,2,3-triazole was reacted with (1-Benzyl-1H-indazol-5-yl)-(6-chloro-pyrido[3,4-d]pyrimidin-4yl)-amine as in Example 21 to give the title compound; δH [$^2$H$_6$]DMSO 10.53 (1H,s), 9.28(1H,s), 9.13(1H,s), 8.89(1H,s), 8.64(1H,s), 8.23(1H,s), 8.10(1H,s), 8.00(1H,s), 7.69(2H,s), 7.23(5H,m), 5.62(2H,s); m/z (M$^+$) 420.

Example 24

(1-Benzyl-1H-indazol-5-yl)-(6-pyrrolidin-1-yl-pyrido[3,4]pyrimidin-4-yl)-amine

Pyrrolidine (2 ml) was reacted with (1-Benzyl-1H-indazol-5-yl)-(6-chloro-pyrido[3,4-d]pyrimidin-4-yl)-amine (0.4 g) in a reacti-vial at 100° c. (Procedure C). After 18 hours, the cooled mixture was poured onto water and the precipitate washed with hot ether and crystallised from acetone to give the title compound; δH [$^2$H$_6$]DMSO 10.53 (1H,s), 9.75(1H,s), 8.79(1H,s), 8.30(1H,s), 8.23(1H,s), 8.14 (1H,s), 7.70(2H,m), 7.28(5H,m), 7.14(1H,s), 5.68(2H,s), 3.50(4H,m), 2.02(4H,m); m/z (M$^+$) 422.

Example 25

(1-Benzyl-1H-indazol-5-yl)-(6-piperidin-1-yl-pyrido[3,4]pyrimidin-4-yl)-amine

Piperidine was reacted with (1-Benzyl-1H-indazol-5-yl)-(6-chloro-pyrido[3,4-d]pyrimidin-4-yl)-amine as in Example 24 to give the title compound (Procedure C); δH [$^2$H$_6$]DMSO 9.80 (1H,m), 8.80(1H,s), 8.33(1H,s), 8.22(1H,s), 8.15(1H,s), 7.70(2H,m), 7.50(1H,s), 7.28(5H,m), 5.68 (2H,s), 3.65(4H,m), 1.65(6H,m); m/z (M$^+$) 436.

Example 26

N4-(1-Benzyl-1H-indazol-5-yl)-(6-piperidin-1-yl)-pyrido[3,4]pyrimidin-4,6-diamine Ethylmethylamine was reacted with (1-Benzyl-1H-indazol-5-yl)-(6-chloro-pyrido[3,4-d]pyrimidin-4-yl)-amine as in Example 2 to give the title compound (Procedre C); δH [$^2$H$_6$]DMSO 9.87 (1H,s), 8.86(1H,s), 8.37(1H,s), 8.25(1H,s), 8.20(1H,s), 7.76(2H,m), 7.35(5H,m), 5.75(2H,s), 3.79 (2H,q), 3.18(3H,s), 1.19(3H,t); m/z (M$^+$) 410.

Example 27

2-(4-(4-(1-Benzyl-1H-indazol-5-ylamino)-pyrido[3,4-d]pyrimidin-6-yl)-piperazin-1-yl)-N-isopropyl-acetamide 4-Isopropylacetamido-1,4-piperazine (Aldrich) was reacted with (1-Benzyl-1H-indazol-5-yl)-(6-chloro-pyrido[3,4-d]pyrimidin-4-yl)-amine as in Example 24 to give the title compound (Procedure C); δH [$^2$H$_6$]DMSO 8.35(1H,s), 8.20(1H,d), 7.72(2H,m), 7.55(1H,s), 7.30(5H,m),5.70(2H,s) 3.95(1H,m), 3.68(4H,bs), 3.00(2H,s), 2.60(4H,bs), 1.10(5H,d); m/z (M$^+$) 535.

Example 28

2-(4-(4-(1-Benzyl-1H-indazol-5-ylamino)-pyrido[3,4-d]pyrimidin-6-yl)-piperazin-1-yl)-1-morpholin-4-yl-ethanone N-Morpholinylacetamido-1,4-piperazine (Emkachem) was reacted with (1-Benzyl-1H-indazol-5-yl)-(6-chloro-pyrido[3,4-d]pyrimidin-4-yl)-amine as in Example 24 to give the title compound (Procedure C); δH [$^2$H$_6$]DMSO 9.80(1H,s), 8.83(1H,s), 8.38(1H,s), 8.22(1H,s), 8.15(1H,s), 7.75(1H,d) 7.66(1H,dd),7.55(1H,s), 7.28(5H,m), 5.70(2H,s), 3.60(10H,m), 3.50(2H,m), 3.28(3H,s), 2.62(4H,bs); m/z (M$^+$) 564.

Example 29

(1-Benzyl-1H-indazol-5-yl)-(6-(5-methyl-1,3,4-oxadiazol-2-yl)-pyrido[3,4-d]pyrimidin-4-yl)-amine hydrochloride 4-Chloro-6-(5-methyl-1,3,4-oxadiazol-2-yl) pyrido[3,4-d]pyrimidine (0.02 g) was reacted with 1-benzylindazol-5-ylamine according to Procedure A to give the title compound as a yellow solid; δH [$^2$H$_6$]DMSO 11.50(1H,s), 9.55(1H,s), 9.43(1H,s), 8.95(1H,s), 8.34(2H,m),7.91(1H,d) 7.83(1H,dd),7.40(5H,m), 5.80(2H,s), 2.75 (3H,s); m/z (M+1$^+$) 435.

Example 30

(1-(3-Fluoro-benzyl)-1H-indazol-5-yl)-(6-(5-methyl-1,3,4-oxadiazol-2-yl)-pyrido[3,4-d]pyrimidin-4-yl)-amine hydrochloride Prepared according to Procedure A from 1-(3-Fluoro-benzyl)-1H-indazol-5-ylamine and 4-chloro-6-(5-methyl-1,3,4-oxadiazol-2-yl)-pyrido[3,4-d]pyrimidine; δH [$^2$H$_6$]DMSO 11.50(1H,s), 9.53(1H,s), 9.41(1H,s), 8.94(1H,s), 8.30(2H,s), 7.90(1H,d), 7.80(1H,dd), 7.45(1H,d),7.25(3H,m) 5.80(2H,s), 2.75 (3H,s); m/z (M+1$^+$) 453.

Example 31

(1-Benzyl-1H-indazol-5-yl)-(6-chloro-pyrido[3,4-d]pyrimidin-4-yl)-amine hydrochloride Prepared according to Procedure A from 1-benzyl-1H-indol-5-ylamine and 4,6-dichloro-pyrido[3,4-d]pyrimidine;

δH [²H₆]DMSO 11.45(1H,s), 9.08(1H,s), 8.95(1H,s), 8.80 (1H,s), 7.98(1H,d), 7.60(2H,m), 7.30(6H,m), 6.60(1H,d), 5.48(2H,s); m/z (M+1⁺) 386.

Example 32

(1-Benzyl-1H-indazol-5-yl)-(6-(4-methyl-piperazin-1-yl)-pyrido[3,4-d]pyrimidin-4-yl)-amine 4-Methylpiperazine was reacted with (1-Benzyl-1H-indazol-5-yl)-(6-chloro-pyrido[3,4-d]pyrimidin-4-yl)-amine as in Example 24 to give the title compound (Procedure C); δH [²H₆]DMSO 9.80(1H,s), 8.82(1H,s), 8.47(1H,s), 8.23 (1H,s), 8.15(1H,s), 7.75(1H,d), 7.67(1H,d), 7.54(1H,s), 7.28 (5H,m), 5.68(2H,s) 3.64(4H,m), 3.34(4H,m), 2.27(3H,s); m/z (M⁺) 451.

Example 33

(1-Benzyl-1H-indazol-5-yl)-(6-benzyloxy-pyrido[3,4-d]pyrimidin-4-yl)-amine hydrochloride 6-Benzyloxy-4-chloro-pyrido[3,4-d]pyrimidine (0.54 g, ca. 2 mmol) and 5-amino-1-benzyl-1H-indazole (0.458 g, 2.05 mmol) were reacted according to Procedure A to give the title compound as a yellow solid (0.740 g, 1.50 mmol, 75%); δH [²H₆]DMSO 11.50(1H,s), 9.00(1H,s), 8.77(1H,s), 8.16–8.33 (3H,m), 7.83(1H,d), 7.71 (1H,dd), 7.13–7.58 (10H,m), 5.69(2H,s), 5.55(2H,s); m/z (M+1⁺) 459.

Example 34

(1-Benzyl-1H-indazol-5-yl)-(6-(5-((2-methanesuphonyl-ethylamino)-methyl)-furan-2-yl)-pyrido-[3,4-d]pyrimidin-4-yl)-amine hydrochloride 5-(4-(1-Benzyl-1H-indazol-5-ylamino)-pyrido[3,4-d] pyrimidin-6-yl)-furan-2-carbaldehyde (0.70 g, 1.81 mmol), 2-(methanesulphonyl)ethylamine hydrochloride (1.30 g, 8.14 mmol) and triethylamine (0.65 ml,0.47 g, 4.7 mmol) were stirred in dichloromethane (7 ml) at room temperature for 1 hour forming a precipitate. The mixture was cooled to 0° c. and sodium triacetoxyborohydride (1.60 g, 7.5 mmol) was added. The temperature was maintained at 0° C. for 15 min and then stirring was continued at room temperature overnight. The reaction mixture was diluted with water, and the resulting pale yellow preciptate was collected and washed with water and acetone. This was resuspended in a mixture of acetone and methanol and acidified with ethereal HCl. The solvents were removed in vacuo and the residue suspended in acetone and collected by filtration. This was dried at 60° c. in vacuo to give the product as an orange-yellow solid (0.40 g, 0.64 mmol, 35%); δH [²H₆]DMSO 11.40(1H,s), 9.88(1H,br s), 9.52(1H,s), 9.22 (1H,s), 8.80 (1H,s), 8.31 (1H,s), 8.19 (1H,s), 7.77–7.90 (2H,m), 7.21–7.37 (6H,m), 6.98 (1H,d), 5.70 (2H,s), 4.47 (2H,d), 3.42–3.80 (4H,m, obscured by water), 3.14 (3H,s); m/z (M+1⁺) 554.

Example 35

(5[4(1-Benzyl-1H-indazol-5-ylamino)-pyrido-[3,4-d]pyrimidin-6-yl)-furan-2-carboxylic acid hydrochloride (1-Benzylindazol-5-yl)-(6-(5-(4-methyl-2,6,7-trioxabicyclo[2,2,2]oct-1-yl)-furan-2-yl]-pyrido-[3,4-d]pyrimidin-4-yl)-amine (0.445 g, 0.81 mmol) was suspended in a mixture of THF (15 ml) and dilute HCl (15 ml) and stirred at room temperature for 18 hours. The mixture was diluted with water to preciptate the intermediate (partial hydrolysis) which was collected by filtration and washed with water. This solid was suspended in a mixture of THF (10 ml) and NaOH (1M, 10 ml) and stirred at room tmperature for 18 hours. The THF was removed in vacuo and the residue was acidified to pH1 with dilute HCl to give the product as an orange solid, which was collected by filtration (0.322 g, 0.645 mmol, 79%); δH [²H₆]DMSO 10.63(1H,s), 9.19(1H,s), 8.89(1H,s), 8.64 (1H,s), 8.17–8.22 (2H,m), 7.67–7.80 (2H,m), 7.46 (1H,s), 7.23–7.39 (6H,m), 5.70 (2H,s); m/z (M+1⁺) 463.

Example 36

(5[4(1-Benzyl-1H-indazol-5-ylamino)-pyrido-[3,4-d]pyrimidin-6-yl]-furan-2-carboxylic acid 2-methanesulphonyl-ethylamide hydrochloride 5-[4-(1-Benzyl-1H-indazol-5-ylamino)-pyrido-[3,4-d] pyrimidin-6-yl]-furan-2-carboxylic acid hydrochloride (0.125 g, 0.25 mmol) and carbonyl diimidazole (0.052 g, 0.33 mmol) were suspended in dry THF (3 ml) under a nitrogen atmosphere and stirred at room temperature for 7 hours. 2-(Methanesulphonyl)ethylamine hydrochloride (0.080 g, 0.50 mmol) and triethylamine (0.15 ml, 0.11 g, 1.08 mmol) were added, together with further THF (2 ml), and the resulting mixture was stirred at room temperature for 18 hours. The mixture was absorbed onto silica gel and purified by column chromatography, eluting with 2–10% MeOH/DCM. Concentration of the relevant fractions gave a pale yellow solid. This was resuspended in methanol and treated with ethanolic HCl to give the product as an orange solid, which was collected by filtration, washed with methanol, acetone and ether, and dried in vacuo (0.093 g, 0.154 mmol, 61%); δH [²H₆]DMSO 12.00(1H,s), 9.76(1H, s), 9.19–9.29 (2H,m), 8.75 (1H,s), 8.28 (1H,s), 8.22 (1H,s), 7.78–7.90 (2H,m), 7.23–7.38 (7H,m), 5.71 (2H,s), 3.50–3.90 (2H obscured by water signal), 3.48 (2H,t), 3.07 (3H,s); m/z (M+1⁺) 568.

Examples 37 and 38

N4-(1-Benzyl-1H-indazol-5-yl)-N6-methyl-pyrido [3,4-d]pyrimidine-4,6-diamine;

N4-[1-(4-Hydroxybenzyl)-1H-indazol-5-yl)-N6,N6-dimethyl-pyrido[3,4-d]pyrimidine-4,6-diamine Prepared by incubation of N4-(1-Benzyl-1H-indazol-5-yl)-N6,N6-dimethyl-pyrido[3,4-d]pyrimidine-4,6-diamine with *Streptomyces rimosus subsp. paromomycinus* (NRRL 2455). The micro-organism was stored frozen (−80° C.) on porous beads in cryovials containing cryopreservative (Microbank™ beads, Richmond Hill, Ontario, Canada). A single bead was used to inoculate each of 2×50 ml aliquots of culture medium (SB1) dispensed in 250 ml Erlenmeyer flasks.

The microorganism was grown in SB1 medium at a temperature of 28° C. Flasks were shaken at 250 rpm. The SB1 culture medium consisted of Arkasoy (25 g; British Arcady Company), Bacto yeast extract (5 g; Difco Laboratories) and $KH_2PO_4$ (5 g) in distilled water (900 ml). The pH of the culture medium was adjusted to 7.2 using conc. NaOH prior to autoclaving (15 min./121° C.) 100 ml of a 20% (w/v) solution of glucose (filter sterilised) was added post sterilisation.

N4-(1-Benzyl-1H-indazol-5-yl)-N6,N6-dimethyl-pyrido [3,4-d]pyrimidine-4,6-diamine (12.5 mg) in methanol (1.0 ml) was added to each culture flask after 72 hours growth. Cultures were harvested 7 days after compound addition.

Isolation: The culture broth (2×50 ml) was mixed with an equal volume of methanol (containing 0.6% (v/v) TFA), centrifuged (4000 rpm, 4C, 30 min) and the supernatant concentrated under a stream of nitrogen gas. The resulting concentrated aqueous extract was adsorbed onto a water-equilibrated C18 SPE cartridge (2 g; Varian Ltd., Walton-on Thames, UK) which was washed with water (5 volumes), then eluted with 3×5 ml methanol (containing 0.3% (v/v) TFA). The eluent was then diluted (mobile phase A, 10 ml) and filtered (0.2 mm PTFE filter) prior to preparative HPLC using the following system: —Spherisobr SB5 C6 15 cm×20 mm, flow rate 20 ml/min, detection wavelength 232 nm; mobile phase A: 50 mM ammonium acetate containing 3 ml/l TFA; mobile phase B: 50% acetonitrile, 50 mM ammonium acetate containing 3 ml/l TFA; gradient: 0 to 30 min, 100%A—100%B; 30 to 35 min, 100%B; 35 to 37 min, 100%B—100%A; 37 to 40 min, 100%A. Appropriate fractions were absorbed onto water-equilibrated C18 SPE cartridges (200 mg; Varian Ltd., Walton-on-Thames, UK), which were washed with water (5 volumes) then eluted with 2×1 ml methanol (containing 0.3% (v/v) TFA). The solvent was removed in vacuo to yield the title compounds.

From the incubation was obtained:

N4-(1-Benzyl-1H-indazol-5-yl)-N6-methyl-pyrido[3,4-d]pyrimidine-4,6-diamine (0.9 mg); $\delta$H [$^2$H$_6$]DMSP 10.95 (1H,s), 8.79(1H,s), 8.63 (1H,s), 8.21 (1H,s), 8.15 (1H,s), 7.82 (1H,d), 7.67 (1H,d), 7.20–7.38 (6H,m), 5.71 (2H,s), 2.91 (3H,s); and N4[1-(4-Hydroxybenzyl)-1H-indazol-5-yl)-N6,N6-dimethyl-pyrido[3,4-d]pyrimidine-4,6-diamine (1.5 mg); $\delta$H[$^2$H$_6$]DMSO 11.30 (1H,s), 9.55 (1H,br s), 8.89 (1H,s), 8.73 (1H,s), 8.20 (1H,s), 8.09 (1H,s), 7.84 (1H,d), 7.64 (1H,d), 7.50 (1H,s), 7.17 (2H,d), 6.71 (2H,d), 5.58 (2H,s), 3.20 (6H,s).

Examples 39 to 41

The following compounds (and their hydrochlorides, if appropriate) are prepared by analogous techniques using the approprite starting materials:

N4-[1-(S,R-α-Methylbenzyl)-1H-indazol-5-6l]-N6,N6-dimethyl-pyrido-[3,4-d]pyrimidin-4,6-diamine;

N4-(3Benzylsulphonyl-1H-indazol-6-yl)-N6,N6-dimethyl-pyrido[3,4-d]-pyrimidine-4,6-diamine;

N4-(3-Benzyl-1H-indazol-6-yl)-N6,N6-dimethyl-pyrido[3,4-d]-pyrimidine-4,6-diamine.

Biological Data

Compounds of the present invention were tested for protein tyrosine kinase inhibitory activity in substrate phosphorylation assays and cell proliferation assays.

The substrate phosphorylation assays use baculovirus expressed, recombinant constructs of the intracellular domains of c-erbB-2 and c-erbB-4 that are constitutively active and EGFr isolated from solubillised A431 cell membranes. The method measures the ability of the isolated enzymes to catalyse the transfer of the γ-phosphate from ATP onto tyrosine residues in a biotinylated synthetic peptide (Biotin-GluGluGluGlu TyrPheGluLeuVal). The enzyme is incubated for 30 minutes, at room temperature, with 10 mM MnCl$_2$, ATP and peptide at Km concentrations, and test compound (diluted from a 5 mM stock in DMSO, final DMSO concentration is 2%) in 40 mM HEPES buffer, pH 7.4. The reaction is stopped by the addition of EDTA (final concentration 0.15 mM) and a sample is transferred to a streptavidin-coated 96-well plate. The plate is washed and level of phosphotyrosin on the peptide is determined using a Europium-labelled antiphosphotyrosine anitbody and quantified with a time-resolved fluorescence technique. The results are shown in Table 1 as the IC$_{50}$ values in nM.

The cell proliferation assay uses an immortalised human breast epithelial cell line (HB4a) which has been transformed by over-expression of c-erbB-2. Growth of these cells in low serum is dependent upon the c-erbB-2 tyrosine kinase activity. The specificity of the effect of the test compounds on tyrosine kinase dependent growth over general toxicity is assessed by comparison to an HB4a cell line which has been transfected with ras. Cells are plated at 3000/well in 96-well plates in 0.1 ml medium and allowed to attach overnight. test compound is added in 0.1 ml medium, with a final concentration of 0.5% DMSO, and the plates incubated for 4 days at 37° C. The cells are then examined microscopically for evidence of morphological detransformation and cell mass is estimated by staining with methylene blue and measuring the absorbance at 620 nm. The results are shown in Table 1 below as the IC$_{50}$ values in nM. Activity against a range of naturally occurring EGFr or c-erbB-2 over-expressing human tumour cell lines (BT474-breast, HN5-head and neck, N87-gastric and Calu3-lung) is assessed with selected compounds by the same methodology. The results are also shown in Table 1 below as the IC$_{50}$ values in nM.

TABLE 1

| Example | Substrate Phosphorylation | | | Cell Proliferation | | | | | |
|---|---|---|---|---|---|---|---|---|---|
| | EGFr | erbB-2 | erbB-4 | HB4a erbB-2 | HB4a ras | BT474 | N87 | Calu3 | HN5 |
| 1 | | 27 | 48 | | | | | | |
| 2 | 1 | 19 | 20 | 110 | 17000 | 140 | 240 | 380 | 300 |
| 3 | | 7 | 23 | 140 | 33000 | | | 1800 | |
| 4 | | 120 | 1300 | 3900 | 13000 | | | | |
| 6 | | 11 | 150 | | | | | | 320 |
| 7 | | 7 | 21 | 1900 | 19000 | 610 | | 8000 | |
| 10 | | 6 | 10 | 71 | 21000 | 2 | 2 | 160 | 130 |
| 11 | 15 | 9 | 55 | 1400 | 3800 | 1400 | 370 | 1200 | 1400 |
| 12 | 77 | 1 | 3 | 170 | 32000 | | | | |
| 13 | 370 | 50 | 2400 | 240 | 28000 | | | | |
| 14 | 830 | 430 | 1500 | 950 | 7900 | | | | |
| 15 | | 7 | 4 | 4 | 14000 | | | | |
| 16 | | 9 | 96 | 44 | 11000 | 1 | 120 | 180 | 81 |
| 17 | | 250 | | 490 | 7600 | 550 | | 7000 | |

TABLE 1-continued

| | Substrate Phosphorylation | | | Cell Proliferation HB4a | | | | | |
|---|---|---|---|---|---|---|---|---|---|
| Example | EGFr | erbB-2 | erbB-4 | HB4a erbB-2 | HB4a ras | BT474 | N87 | Calu3 | HN5 |
| 18 | 290 | 98 | 1700 | 21 | 19000 | | | | 440 |
| 19 | 540 | 6 | 130 | 1200 | 33000 | | | | |
| 20 | 4 | 33 | | 470 | 14000 | | | | |
| 21 | 54 | | | 500 | 18000 | | | | |
| 22 | 22 | | | 1700 | 18000 | | | | |
| 23 | 31 | | | 250 | 22000 | | | | |
| 24 | | 20 | 140 | 810 | 50000 | 460 | | | 900 |
| 25 | 380 | 60 | 570 | 480 | >50000 | 270 | 940 | | |
| 26 | 54 | 29 | | 150 | 8900 | | | | |
| 27 | | 2 | 190 | 380 | 21000 | | | | |
| 28 | | 4 | 170 | 590 | 28000 | | | | |
| 29 | 2 | 2 | 5500 | 5200 | 29000 | 11000 | 10000 | | |
| 30 | 2 | 2 | 9600 | 2900 | 26000 | | | | |
| 32 | | 55 | 140 | 100 | 8800 | 1000 | 600 | 8200 | 4200 |
| 33 | 1900 | 140 | 2700 | >50000 | 50000 | | | | |
| 34 | | 15 | 230 | 70 | 17000 | 2 | 190 | 1300 | 190 |
| 35 | 1600 | | | 27000 | >50000 | | | | |
| 36 | 1600 | | | 3100 | >50000 | | | | |
| 37 | 30 | 65 | 180 | 520 | 17000 | 1100 | 2200 | 3700 | 2000 |
| 38 | 930 | 330 | 1900 | 6900 | 50000 | | | | |

What is claimed is:

1. A compound of formula (I):

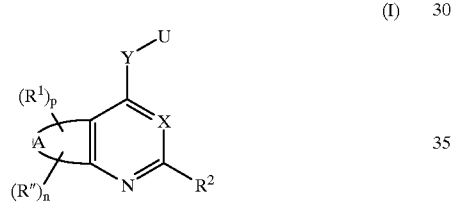

(I)

or a salt or solvate thereof;
wherein X is N;
Y is a group $W(CH_2)$, $(CH_2)W$, or W, in which W is O, $S(O)_m$ wherein m is 0, 1 or 2, or $NR^a$ wherein $R^a$ is hydrogen or a $C_{1-8}$alkyl group;
either
n is 1, p is 0 and R" is selected from the group consisting of phenyl, furan, thiophene, pyridine, pyrimidine, pyrazine, pyrrole, oxazole, isoxazole, oxadiazole, thiazole, isothiazole, triazole, tetrazole, and imidazole or a hydrogenated derivative thereof, said group being optionally substituted by one or more $R^1$ groups; wherein $R^1$ is either
selected from $M^1$–$M^2$–$M^3$–$M^4$, $M^1$–$M^5$ or $M^1$–$M^2$–$M^{3'}$–$M^6$, or j
selected from the group consisting of amino, hydrogen, halogen, hydroxy, hydroxy-$C_{1-4}$alkyl, formyl, carboxy, cyano, nitro, $C_{1-8}$alky, $C_{1-8}$alkoxy, $C_{1-8}$alkylthio, $C_{1-8}$alkylsulphinyl, $C_{1-8}$alkylsulphonyl, $C_{1-4}$alkylamino, $C_{1-4}$dialkylamino, dioxolanyl, or hydroxy-$C_{1-4}$alkanoyl-($C_{1-4}$alkyl)-amino; or
n is 0, p is 0, 2, or 3 and each $R^1$ is selected from the group consisting of amino, hydrogen, halogen, hydroxy, hydroxy-$C_{1-4}$alkyl, formyl, carboxy, cyano, nitro, $C_{1-8}$alkyl, $C_{1-8}$alkoxy, $C_{1-8}$alkylthio, $C_{1-8}$alkylsulphinyl, $C_{1-8}$alkylsulphonyl, $C_{1-4}$alkylamino, $C_{1-4}$dialkylamino, dioxolanyl, benzyloxy, or hydroxy-$C_{1-4}$alkanoyl-amino; or when p is 2 or 3, two adjacent $R^1$ groups together form an optionally substituted methylenedioxy or ethylenedioxy group; or
n is 0, p is 1 and $R^1$ is
selected from $M^1$–$M^2$–$M^3$–$M^4$, $M^1$–$M^5$ or $M^1$–$M^2$–$M^{3'}$–$M^6$; or
selected from the group consisting of amino, hydrogen, halogen, hydroxy, hydroxy-$C_{1-4}$alkyl, formyl, carboxy, cyano, nitro, $C_{1-8}$alkyl, $C_{1-8}$alkylthio, $C_{1-8}$alkylsulphinyl, $C_{1-8}$alkylsulphonyl, $C_{1-4}$alkylamino, $C_{1-4}$dialkylamino, dioxolanyl, benzyloxy, or hydroxy-$C_{1-4}$alkanoyl-($C_{1-4}$alkyl)-amino;

$M^1$ represents a $C_{1-4}$alkyl group, wherein optionally a $CH_2$group is replaced by a CO group;

$M^2$ represents a $NR^{12}$ or $CR^{12}R^{13}$, in which $R^{12}$ and $R^{13}$ each independently represent H or $C_{1-4}$alkyl;

$M^3$ represents a $C_{1-4}$alkyl group;

$M^{3'}$ represents a $C_{1-4}$alkyl group or is absent;

$M^4$ represents CN, $NR^{12}S(O)_mR^{13}$, $S(O)_mNR^{14}R^{15}$, $CONR^{14}R^{15}$, $S(O)_mR^{13}$ or $CO_2R^{13}$, in which $R^{12}$, $R^{13}$ and m are as hereinbefore defined and $R^{14}$ and $R^{15}$ each independently represent H or $C_{1-4}$alkyl, or $R^{14}$ and $R^{15}$ together with the nitrogen atom to which they are attached represent a 5- or 6-membered ring optionally containing 1 or 2 additional heteroatoms selected from N, O or $S(O)_m$ in which ring any nitrogen atom present may optionally be substituted with a $C_{1-4}$alkyl group;

$M^5$ represents the group $NR^{14}R^{15}$ or the group

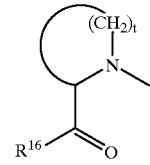

and $M^6$ represents a $C_{3-6}$ cycloalkyl group, the group $NR^{14}R^{15}$ or a 5- or 6-membered heterocyclic ring system containing 1 to 4 heteroatoms selected from N, O or S;

$R^2$ represents hydrogen;

U represents an indolyl, isoindolyl, indolinyl, isoindolinyl, 1H-indazolyl, 2,3-dihydro-1H-indazoylyl, 1H-benzimidazoylyl, 2,3-dihydro-1H-benimidazoylyl or 1H-benzotriazoylyl group which is substituted by at least one independently selected $R^6$ group and is optionally substituted by at least one independently selected $R^4$ group, each $R^4$ is independently hydrogen, hydroxy, halogen, $C_{1-4}$alkyl, $C_{1-4}$alkoxy, $C_{1-4}$alkylamino, di-amino, $C_{1-4}$alkylthio, $C_{1-4}$alkylsulphinyl, $C_{1-4}$alkylsulphonyl, $C_{1-4}$alkylcarbonyl, $C_{1-4}$alkylcarbamoyl, di-carbamoyl, carbamyl, $C_{1-4}$alkoxycarbonyl, cyano, nitro or trifluoromethyl;

each $R^6$ is independently benzyl, halo-, dihalo- and trihalobenzyl, α-methylbenzyl, phenyl, halo-, dihalo-, and trihalophenyl, pyridyl, pyridylmethyl, pyridyloxy, pyridylmethoxy, thienylmethoxy, dioxolanylmethoxy, cyclohexylmethoxy, phenoxy, halo-dihalo-, and trihalophenoxy, phenylthio, benzyloxy, halo-, dihalo-, trihalobenzyloxy, $C_{1-4}$alkoxybenzoyloxy, phenyloxalyl or benzenesulphonyl; and A represents

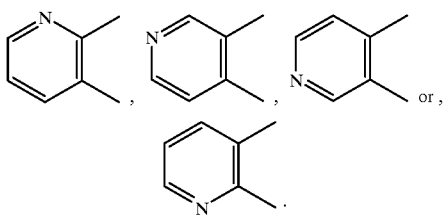

2. A compound as claimed in claim 1 wherein Y is $NR^a$, $NR^a(CH_2)$, or $(CH_2)NR^a$.

3. A compound as claimed in claim 1 wherein n is 0 and each $R^1$ is selected from the group comprising amino, $C_{1-4}$alkylamino, di-$C_{1-4}$alkylamino.

4. A compound as claimed in claim 1 wherein n is 0, p is 1 and $R^1$ is selected from the group comprising amino, $C_{1-4}$alkylamino, di$C_{1-4}$alkylamino.

5. A compound as claimed in claim 1 wherein $M^1$ represents $CH_2$, CO, $CH_2CH_2$ or $CH_2CO$; $M^2$ represents $NR^{12}$ in which $R^{12}$ is as defined in claim 1; $M^3$ represents $CH_2$, $CH_2CH_2$ or propyl; $M^{3'}$ represents $CH_2$, ethyl, propyl, isopropyl or is absent; $M^4$ represents $SOR^{13}$, $SO_2R^{13}$, $NR^{12}SO_2R^{13}$ or $CONR^{14}R^{15}$ in which $R^{12}$ and $R^{13}$ are defined in claim 1 and $R^{14}$ and $R^{15}$ each independently represent H or $C_{1-4}$alkyl; $M^5$ represents a group $NR^{14}R^{15}$ in which $R^{14}$ and $R^{15}$ together with the nitrogen atom to which they are attached represents a 6-membered ring optionally containing an additional heteroatom selected from N or O, wherein said heteroatom may optionally be substituted with a $C_{1-4}$alkyl group when it represents N; or $M^5$ represents a group

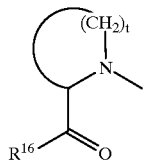

in which t represents 2 or 3 and $R^{16}$ represents OH, $NH_2$, $N(C_{1-4}$alkyl$)_2$ or $OC_{1-4}$alkyl; or $M^5$ represents a group $NR^{14}R^{15}$ in which $R^{14}$ and $R^{15}$ each independently represent hydrogen or $C_{1-4}$alkyl; and $M^6$ represents a group $NR^{14}R^{15}$ in which $R^{14}$ and $R^{15}$ each independently represent $C_{1-4}$alkyl; or $R^{14}$ and $R^{15}$ together with the nitrogen atom to which they are attached represent a 5- or 6-membered ring optionally containing an additional heteroatom selected from N or O, wherein any N atom present in the 5- or 6-membered ring may optionally be substituted with a $C_{1-4}$alkyl group; or $M^6$ represents a 5- or 6-membered heterocyclic ring system containing 1 or 2 heteroatoms selected from N or O.

6. A compound as claimed in claim 1 wherein $M^2$–$M^3$–$M^4$ together represents an α-amino carboxylic acid or a methyl ester or amide thereof; or $M^2$–$M^3$–$M^4$ represents a β-or γ-amino sulphinic or sulphonic acid or a methyl ester therof.

7. A compound as claimed in claim 1 wherein $M^2$–$M^3$–$M^4$ together represents a methylsulphonylethylamino, methylsulphinylethylamino, methylsulphonylpropylamino, methylsulphinylpropylamino, methylsulphonamidoethylamino, sarcosinamide, glycine, glycinamide, or glycine methyl ester group.

8. A compound as claimed in claim 1 wherein $M^1$–$M^5$ together represents a piperaziinyl-methyl, methylpiperazinyl-methyl, piperidinyl-methyl, prolinamidomethyl, N,N-dimethylprolinamido-methyl, isopropylacetamido or N-morpholinoacetamido group.

9. A compound as claimed in claim 1 wherein R" is selected from the group comprising phenyl, furan, imidazole, tetrazole, pyrrolidine, piperazine, piperidine and oxadiazole.

10. A compound as claimed in claim 1 wherein $R^6$ is benzyl, fluorobenzyl, benzyloxy, fluorobenzyloxy, pyridylmethyl, phenyl, benzenesulphonyl, phenoxy or fluorophenoxy.

11. A compound as claimed in claim 1 wherein A represents a pyridine ring; and either (a) p is 0; n is 1; and the group R" is in the 6-position of the pyridopyrimidine ring system or (b) n is 0; p is 1; and the group $R^1$ is in the 6-position of the pyridopyrimidine ring system.

12. A compound of forumula (I) or a salt or solvate thereof as claimed in claim 1 wherein X represents N; Y represents $NR^a$, wherein $R^a$ is hydrogen or $C_{1-4}$alkyl; A represents a pyridine ring; R" is as defined in claim 1 optionally substituted by one or more $R^1$ groups selected from halo, $C_{1-4}$alkyl, cqrboxy, formyl, hydroxy-$C_{1-4}$alkyl, 1,3-dioxolan-2-yl, amino, $C_{1-4}$alkylamino, di($C_{1-4}$alkyl)amino, hydroxy-$C_{1-4}$alkanoyl($C_{1-4}$alkyl)amino, $C_{1-4}$alkylamino-$C_{1-4}$alkyl or di($C_{1-4}$alkyl)amino-$C_{1-4}$alkyl; p is 0; $R^2$ represents hydrogen; $R^4$ represents hydrogen or methyl; U represents indolyl, benzimidazolyl or indazolyl; and $R^6$ represents phenyl, benzyl, α-methylbenzyl, fluorobenzyl, benzenesulphonyl, phenoxy, fluorophenoxy, benzyloxy or fluorobenzyloxy.

13. A compound of formula (I) or a salt or solvate thereof as claimed in claim 1 wherein Y represents $NR^a$, wherein $R^a$ is hydrogen or $C_{1-4}$alkyl; A represents a pyridine ring, R" is as defined in claim 1 optionally substituted with an $R^1$ group selected from methylsulphonylethylaminomethyl, methylsulphonylethylamino-carbonyl, methylsulphinylethylamino-methyl, methylsulphinylethylamino-carbonyl, methylsulphonylpropylamino-methyl, methylsulphinylpropylamino-methyl, methylsulphonylpropyamino-carbonyl methylsulphinylethylamino-carbonyl, methylsulphonylethyl-(methylamino)-methyl, methylsulphonylethyl-(methylamino)-carbonyl, methylsulphinylethyl-(methylamino)-methyl, methylsulphinylethyl-(methylamino)-carbonyl,
methylsulphonylpropyl-(methylamino)-methyl,
methylsulphinylpropyl-(methylamino)-methyl,
methylsulphonylpropyl-(methylamino)-carbonyl,
methylsulphinylpropyl-(methylamino)-carbonyl,
methylsulphonamidoethylamino-methyl,
methylsulphonamidopropylamino-methyl,
sarcosinamidomethyl, glycinylmethyl, glycinamidomethyl, glycinylmethyl methyl ester, acetylaminoethylaminomethyl, piperazinylmethyl, methylpiperazinylmethyl, piperidinylmethyl, N-(proliinamido)methyl, (N,N-dimethylprolinamido)methyl, pyridylaminomethyl, cyclopropylaminomethyl, N-(piperidin-4-yl)-N-methylaminomethyl, N,N-dimethylaminoprop-2-ylaminomethyl, N-(2-dimethylaminoethyl)-N-ethylaminomethyl, isopropylacetamido, N-morpholinylacetamido or tetrahydrofuranomethylaminomethyl and optionally further substituted by one or more $C_{1-4}$alkyl groups; p is 0; $R^2$ represents hydrogen; $R^4$ represents hydrogen or methyl; U represents indolyl, benzimidazolyl or indazolyl; and $R^6$ represents phenyl, benzyl, α-methylbenzyl, fluorobenzyl, benzenesulphonyl, phenoxy, fluorophenoxy, benzyloxy or fluorobenzyloxy.

14. A compound of formula (I) or a salt or solvate thereof as claimed in claim 1 wherein Y represents $NR^a$ wherein $R^a$ is hydrogen or $C_{1-4}$alkyl; A presents a pyridine ring; n is 0; each $R^1$ group is selected from hydrogen, halo, $C_{1-4}$alkyl, carboxy, formyl, hydroxy-$C_{1-4}$alkyl, 1,3-dioxolan-2-yl, benzyloxy, amino, $C_{1-4}$alkylamino, di($C_{1-4}$alkyl)amino, hydroxy-$C_{1-4}$alkanoyl($C_{1-4}$alkyl)amino, $C_{1-4}$alkylamino-$C_{1-4}$alkyl, di($C_{1-4}$alkyl)amino-$C_{1-4}$alkyl, methylsulphonylethylaminomethyl, methylsulphonylethylamino-carbonyl, methylsulphinylethylamino-methyl, methylsulphinylethylamino-carbonyl, methylsulphonylpropylamino-methyl, methylsulphinylpropylamino-methyl, methylsulphonylpropylamino-carbonyl, methylsulphinylpropylamino-carbonyl methylsulphonylethyl-(methylamino)-methyl, methylsulphonylethyl-(methylamino)-carbonyl, methylsulphinyletrhyl-(methylamino)-methyl, methylsulphinylethyl-(methylamino)-carbonyl, methylsulphonylpropyl-(methylamino)-methyl, methylsulphinylpropyl-(methylamino)-methyl, methylsulphonylpropyl-(methylamino)-carbonyl, methylsulphinylpropyl-(methylamino)-carbonyl, methylsulphonamidoethylamino-methyl, methyl, methylsulphonamidopropylamino-methyl, sarcosinamidomethyl, glycinylmethyl, glycinamidomethyl, glycinylmethyl methyl ester, acetylaminoethylaminomethyl, piperazinylmethyl, methylpiperazinylmethyl, piperidinylmethyl, N-(prolinamido)methyl, (N,N-dimethylprolinamido)methyl, pyridylaminomethyl, cyclopropylaminomethyl, N-(piperidin-4-yl)-N-methylaminomethyl, N,N-dimethylaminoprop-2-ylaminomethyl, N-(2-dimethylaminoethyl)-N-ethylaminomethyl, isopropylacetamido, N-morpholinylacetamido or tetrahydrofuranomethylaminomethyl; $R^2$ represents hydrogen; $R^4$ represents hydrogen or methyl; U represents indolyl, benzimidazolyl or indazolyl; and $R^6$ represents phenyl, benzyl, α-methylbenzyl, fluorobenzyl, benzenesulphonyl, phenoxy, fluorophenoxy, benzyloxy or fluorobenzyloxy.

15. A compound as claimed in claim 12 wherein Y represents $NR^a$, wherein $R^a$ is hydrogen or $C_{1-4}$alkyl; A represents a pyridine ring; R" represents a furan, imidazole, triazole, oxadiazole, pyrrolidine, piperidine or piperazine ring, optionally substituted by one or more $R^1$ groups selected from 1,3-dioxolan-2-yl, formyl, carboxy, $C_{1-4}$alkyl, prolinamidomethyl, isopropylacetamido, N-morpholinylacetamido, methylsulphonylethylaminomethyl or methylsulphonylethylaminocarbonyl; p is 0; $R^2$ represents hydrogen; $R^4$ represents hydrogen or methyl; U represents indazolyl, indolyl or benzimidazolyl; and $R^6$ represents benzyl, fluorobenzyl, pyridylmethyl or benzenesulphonyl.

16. A compound as claimed in claim 15 wherein Y represents $NR^a$, wherein $R^a$ is hydrogen or $C_{1-4}$alkyl; A represents a pyridine ring; n is 0; each $R^1$ group is selected from hydrogen, halo, benzyloxy, amino, $C_{1-4}$alkylamino, di($C_{1-4}$alkyl)amino or hydroxy-$C_{1-4}$alkanoyl-($C_{1-4}$alkyl)-amino, more preferably dimethylamino; $R^2$ represents hydrogen; $R^4$ represents hydrogen or methyl; U represents indazolyl, indolyl or benzimidazolyl; and $R^6$ represents benzyl, fluorobenzy, pyridylmethyl or benzenesulphonyl.

17. A compound as claimed in claim 1 selected from:

(1-Benzyl-1H-indazol-5-yl)-(6-chloro-pyrido[3,4]pyrimidin-4-yl)-amine;

N4-(1-Benzyl-1H-indazol-5-yl)-N6,N6-dimethyl-pyrido[3,4-d]pyrimidine-4,6-diamine;

(1-Benzyl-1H-indazol-5-yl)-(6(N-(2-hydroxyethyl)-N-methylamino)-pyrido[3,4]pyrimidin-4-yl)-amine;

(1-Benzyl-1H-indazol-5-yl)-(pyrido[3,4]pyrimidin-4-yl)-amine;

(2-Benzyl-1H-benzimidazol-5-yl)-(6-chloro-pyrido[3,4]pyrimidin-4-yl)-amine;

N4-(1-Benzyl-1H-indol-5-yl)-N6,N6-dimethyl-pyrido[3,4-d]pyrimidine-4,6-diamine;

N4-(1-benzimidazol-5-yl)-N6,N6-dimethyl-pyrido[3,4-d]pyrimidine-4,6-diamine;

(1-Benzyl-1H-indazol-5-yl)-(6-(5-[1,3-dioxolan-2-yl]-furan-2-yl)-pyrido[3,4-d]-pyrimidine-4-yl)-amine;

5-(4-(1-Benzyl-1H-indazol-5-ylamino)-pyrido[3,4-d]pyrimidin-6-yl)-furan-2-carbaldehyde;

2S)-1-(5-(4-(1-Benzyl-1H-indazol-5-ylamino)6-pyrido[3,4-d]pyrimidin-6-yl)-furan-2-ylmethyl)-pyrrolidine-2-carboxylic acid amide;

(1Benzyl-1H-indazol-5-yl)-(6-(3-methyl-3H-imidazol-4-yl)-pyrido[3,4-d]pyrimidin-4-yl)-amine;

N6, N6-Dimethyl-N4-(1-pyridin-2-ylmethyl-1H-indazol-5-yl)-pyrido[3,4-d]pyrimidine-4,6-diamine;

N6, N6-Dimethyl-N4-(1-pyridin-3-ylmethyl-1H-indazol-5-yl)-pyrido[3,4-d]pyrimidine-4,6-diamine;

N4-(1-Benzyl-3-methyl-1H-indazol-5-yl)-N6,N6-dimethyl-pyrido[3,4-d]pyrimidine-4,6-diamine;

N4-(1-(2-Fluoro-benzyl)-1H-indazol-5-yl)-N6,N6-dimethyl-pyrido[3,4-d]pyrimidine-4,6-diamine;

N4-(1-(3-Fluoro-benzyl)-1H-indazol-5-yl)-N6,N6-dimethyl-pyrido[3,4-d]pyrimidine-4,6-diamine;

N4-(1-(4-Fluoro-benzyl)-1H-indazol-5-yl)-N6,N6-dimethyl-pyrido[3,4-d]pyrimidine-4,6-diamine;

N4-(1-Benzenesulphonyl-1H-indol-5-yl)-N6,N6-dimethyl-pyrido[3,4-d]pyrimidine-4,6-diamine;

N4-(3-Benzenesulphonyl-1H-indol-5-yl)-N6,N6-dimethyl-pyrido[3,4-d]pyrimidine-4,6-diamine;

(1-Benzyl-1H-indazol-5-yl)-(6-imidazol-1yl-pyrido[3,4-d]pyrimidin-4-yl)-amine;

(1-Benzyl-1H-indazol-5-yl)-(6-(1,2,4-triazol-1-yl-pyrido[3,4-d]pyrimidin-4-yl)-amine;

(1-Benzyl-1H-indazol-5-yl)-(6-(1,2,3-triazol-1-yl-pyrido[3,4-d]pyrimidin-4-yl)-amine;

(1-Benzyl-1H-indazol-5-yl)-(6-(1,2,3-triazol-1-yl-pyrido[3,4-d]pyrimidin-4-yl)-amine;

(1-Benzyl-1H-indazol-5-yl)-(6-pyrrolidin-1-yl-pyrido[3,4-d]pyrimidin-4-yl)-amine;

(1-Benzyl-1H-indazol-5-yl)-(6-piperidin-1-yl-pyrido[3,4-d]pyrimidin-4-yl)-amine;

N4-(1-Benzyl-1H-indazol-5-yl)-N6-ethyl-N6-methyl-pyrido[3,4-d]pyrimidine-4,6-diamine;

2(4-(4-(1-Benzyl-1H-indazol-5-ylamino)-pyrido[3,4-d]pyrimidin-6-yl)-piperazin-1-yl)-N-isopropyl-acetamide;

2(4-(4-(1-Benzyl-1H-indazol-5-ylamino)-pyrido[3,4-d]pyrimidin-6-yl)-piperazin-1-yl)-N-morpholin-4-yl-ethanone;

(1-Benzyl-1H-indazol-5-yl)-(6-(5-methyl-1,3,4-oxadiazol-2-yl)-pyrido[3,4-d]pyrimidin-4-yl)-amine;

(1(3-Fluoro-benzyl)-1H-indazol-5-yl)-(6-(5-methyl-1,3,4-oxadiazol-2-yl)-pyrido[3,4-d]pyrimidin-4-yl)-amine;

(1-Benzyl-1H-indol-5-yl)-(6-chloro-pyrido[3,4-d]pyrimidin-4-yl)-amine;

(1-Benzyl-1H-indazol-5-yl)-(6(4-methyl-piperazin-1-yl)-pyrido[3,4-d]pyrimidin-4-yl)-amine;

(1-Benzyl-1H-indazolyl-5-yl)-(6-benzyloxy-pyrido[3,4-d]pyrimidin-4-yl)-amine;

(1-Benzyl-1H-indazol-5-yl)-(6(5-((2-methanesuphonyl-ethylamino)-methyl)-furan-2-yl)-pyrido[3,4-d]pyrimidin-4-yl)-amine;

5-[4-(1-Benzyl-1H-indazol-5-ylamino)-pyrido-[3,4-d]pyrimidin-6-yl]-furan-2-carboxylic acid;

5-[4-(1-Benzyl-1H-indazol-5-ylamino)-pyrido-[3,4-d]pyrimidin-6-yl]-furan-2-carboxylic acid 2-methanesulphonyl-ethylamide;

N4-(1-Benzyl-1H-indazol-5-yl)-N6-methyl-pyrido[3,4-d]pyrimidine-4,6-diamine;

N4-(4-Hydroxyenzyl)-1H-indazol-5-yl)-N6,N6-dimethyl-pyrido[3,4-d]pyrimidine-4,6-diamine;

and salts or solvates thereof.

18. A compound as claimed in claim 17 selected from:

N4-(1-Benzyl-1H-indazol-5-yl)-N6,N6-dimethyl-pyrido[3,4-d]pyrimidine-4,6-diamine;

N4-(3-Fluoro-benzyl)-1H-indazol-5-yl)-N6,N6-dimethyl-pyrido[3,4-d]pyrimidine-4,6-diamine;

N4-(1-Benzyl-1H-indazol-5-yl)-N6-ethyol-N6-methyl-pyrido[3,4-d]pyrimidine-4,6-diamine;

(1-Benzyl-1H-indazol-5-yl)-(6-(5-((2-methanesuphonyl-ethylamino)-methyl)-furan-2yl)-pyrido[3,4-d]pyrimidine-4-yl-amine;

N4-(1-Benzyl-1H-indazol-5-yl)-N6-methyl-pyrido[3,4-d]pyrimidine-4,6-diamine;

and salts or solvates thereof.

19. A pharmaceutical formulation comprising at least one compound as claimed in claim 1 together with one or more pharmaceutically acceptable carriers, diluents or excipients.

20. A pharmaceutical formulation in unit dosage form containing a compound as claimed in claim 1 in an amount of from 70 to 700 mg.

21. A method of treatment of a human or animal subject suffering from a disorder mediated by aberrant protein tyrosine kinase activity which comprises administering to the human or animal subject an effective amount of a compound as claimed in claim 1.

22. A compound of formula (V)

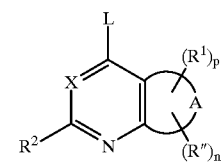

(V)

wherein x, $R^2$ and A are defined in claim 1; n is 0 and p is 0 to 3; each $R^1$ is amino, $C_{1-4}$alkylamino or di-$C_{1-4}$alkylamino;

and L is a leaving group;

provided that the following compounds are excluded:
  4-Chloro-6-(N,N-dimethylamino)-pyrido[3,4-d]pyrimidine;
  6-Amino-4-chloro-pyrido[3,4-d]pyrimidine.

23. A compound of formula (V)

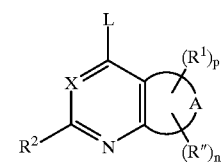

(V)

wherein X, $R^2$ and A are as defined in claim 1; n is 1 and p is 0; and L is a leaving group.

24. A compound of formula (VII)

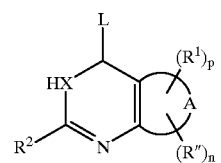

(VII)

wherein X, $R^2$ and A are as defined in claim 1; n is 0 and p is 0 to 3; each $R^1$ is amino, $C_{1-4}$alkylamino or di-$C_{1-4}$alkylamino;

provided that the following compounds are excluded:
  6-(N,N-dimethylamino)-pyrido[3,4-d]pyrimidin-4-one;
  6-Amino-pyrido[3,4-d]pyrimidin-4-one.

25. A compound of formula (VII)

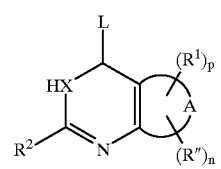

(VII)

wherein X, $R^1$, $R^2$, R" and A are as defined in claim 1; n is 1 and p is 0.

* * * * *

UNITED STATES PATENT AND TRADEMARK OFFICE
CERTIFICATE OF CORRECTION

PATENT NO. : 6,174,889 B1
DATED : January 16, 2001
INVENTOR(S) : Cockerill, et al.

It is certified that error appears in the above-identified patent and that said Letters Patent is hereby corrected as shown below:

Column 43, claim 1,
Line 54, delete "J".
Line 57, delete "$C_{1-8}$ alky" and insert therefor -- $C_{1-8}$ alkyl --.

Column 44, claim 1,
Line 66, insert -- in which t represents 2 to 4 and $R^{16}$ represents OH, $OC_{1-4}$ alkyl or $NR^{14}R^{15}$, --.

Column 45, claim 1,
Line 12, delete "di-amino" and insert therefor -- di($C_{1-4}$ alkyl) amino --.
Line 14, delete "di-carbamoyl" and insert therefor -- di($C_{1-4}$ alkyl) carbamoyl --.

Signed and Sealed this

Sixth Day of November, 2001

Attest:

*Nicholas P. Godici*

NICHOLAS P. GODICI
*Attesting Officer*  *Acting Director of the United States Patent and Trademark Office*